US010801750B2

(12) United States Patent
Radermacher et al.

(10) Patent No.: US 10,801,750 B2
(45) Date of Patent: Oct. 13, 2020

(54) COMFORT UNITS AND SYSTEMS, METHODS, AND DEVICES FOR USE THEREOF

(71) Applicant: University of Maryland, College Park, College Park, MD (US)

(72) Inventors: K. Reinhard Radermacher, Silver Spring, MD (US); Vikrant C. Aute, Jessup, MD (US); Yunho Hwang, Ellicott City, MD (US); Jiazhen Ling, Ellicott City, MD (US); Jelena Srebric, Takoma Park, MD (US); Jan Muehlbauer, Bowie, MD (US); Rohit Dhumane, College Park, MD (US); Yilin Du, Greenbelt, MD (US); Daniel Alejandro Dalgo Reyes, Rockville, MD (US); Nicholas W. Mattise, Hyattsville, MD (US)

(73) Assignee: University of Maryland, College Park, College Park, MD (US)

( * ) Notice: Subject to any disclaimer, the term of this patent is extended or adjusted under 35 U.S.C. 154(b) by 228 days.

(21) Appl. No.: 15/735,538

(22) PCT Filed: Jun. 11, 2016

(86) PCT No.: PCT/US2016/037103
§ 371 (c)(1),
(2) Date: Dec. 11, 2017

(87) PCT Pub. No.: WO2016/201384
PCT Pub. Date: Dec. 15, 2016

(65) Prior Publication Data
US 2018/0120873 A1   May 3, 2018

Related U.S. Application Data

(60) Provisional application No. 62/174,703, filed on Jun. 12, 2015, provisional application No. 62/312,302, (Continued)

(51) Int. Cl.
*F24H 9/18* (2006.01)
*F24F 5/00* (2006.01)
(Continued)

(52) U.S. Cl.
CPC ......... *F24H 9/1854* (2013.01); *F24F 5/0017* (2013.01); *F24H 7/04* (2013.01);
(Continued)

(58) Field of Classification Search
CPC .... F24F 5/0017; F24F 5/0021; F24F 2221/38; F24F 2221/42; F24H 7/04; F24H 7/06;
(Continued)

(56) References Cited

U.S. PATENT DOCUMENTS 2,512,559 A    6/1950  Williams
2,791,401 A    5/1957  Harslem et al.
(Continued)

FOREIGN PATENT DOCUMENTS

DE    38 23 388 A1    1/1990
EP    0 203 437 A2   12/1986
(Continued)

OTHER PUBLICATIONS

Machine Translation of JP10-259942; Retrieved Oct. 24, 2019 (Year: 2019).*

(Continued)

*Primary Examiner* — Eric S Ruppert
*Assistant Examiner* — Hans R Weiland
(74) *Attorney, Agent, or Firm* — Klarquist Sparkman, LLP

(57) ABSTRACT

Despite otherwise uncomfortable conditions in a surrounding environment, a customizable microenvironment can be created around a user to maintain a comfortable temperature and/or humidity level using a comfort unit. For example, the environment may be an office building where conditions are (Continued)

out of the comfortable range to save on energy or for other reasons, a factory/shop environment that is poorly conditioned, or an outdoor location with little to no conditioning. A sensing unit can monitor biometric and environmental data and can determine a comfort level of the user. The comfort unit can then dynamically respond to the determined comfort level and adjust the microenvironment to improve the user's comfort level. The comfort unit can follow the user as the user moves within the macro-environment, or can otherwise move within the macro-environment to achieve certain functions, such as recharging or spatial shifting of thermal load within the overall macro-environment.

23 Claims, 10 Drawing Sheets

Related U.S. Application Data filed on Mar. 23, 2016, provisional application No. 62/312,310, filed on Mar. 23, 2016.

(51) Int. Cl.
*F24H 7/04* (2006.01)
*F24H 7/06* (2006.01)
*F24H 9/20* (2006.01)
*G05D 22/02* (2006.01)
*G05D 23/19* (2006.01)
*A61B 5/01* (2006.01)
*A61B 5/024* (2006.01)
*A61B 5/053* (2006.01)

(52) U.S. Cl.
CPC ............. *F24H 7/06* (2013.01); *F24H 9/2064* (2013.01); *G05D 22/02* (2013.01); *G05D 23/1927* (2013.01); *G05D 23/1928* (2013.01); *A61B 5/01* (2013.01); *A61B 5/024* (2013.01); *A61B 5/0531* (2013.01); *F24F 5/0021* (2013.01); *F24F 2221/38* (2013.01); *F24F 2221/42* (2013.01); *Y02E 60/147* (2013.01)

(58) Field of Classification Search
CPC . F24H 9/1854; F24H 9/2064; G05D 23/1928; G05D 23/1927; G05D 22/02; F28D 20/023; Y02E 60/145; Y02E 60/147
See application file for complete search history.

(56) References Cited

U.S. PATENT DOCUMENTS

| | | | |
|---|---|---|---|
| 4,182,132 A | 1/1980 | Nasser et al. | |
| 4,757,183 A | 7/1988 | Karey et al. | |
| 6,481,213 B2 | 11/2002 | Carr et al. | |
| 6,543,983 B1 | 4/2003 | Felder et al. | |
| 6,647,317 B2 | 11/2003 | Takai et al. | |
| 7,024,876 B1 | 4/2006 | Kishek | |
| 7,152,413 B1* | 12/2006 | Anderson | F24F 5/0017 62/118 |
| 7,298,871 B2 | 11/2007 | Lee et al. | |
| 7,366,588 B2 | 4/2008 | Kim et al. | |
| 8,359,122 B2 | 1/2013 | Koselka et al. | |
| 8,397,529 B2 | 3/2013 | Wolfe, IV et al. | |
| 9,150,081 B2 | 10/2015 | Vreeland et al. | |
| 9,400,510 B2 | 7/2016 | Wang et al. | |
| 9,464,837 B2 | 10/2016 | Wang et al. | |
| 9,518,768 B2 | 12/2016 | Vreeland et al. | |
| 9,546,794 B1* | 1/2017 | Carson | F24F 3/14 |
| 2002/0043068 A1* | 4/2002 | Carr | F24F 5/0017 62/3.7 |
| 2003/0050737 A1 | 3/2003 | Osann | |
| 2004/0011073 A1 | 1/2004 | Blackstone | |
| 2004/0065098 A1* | 4/2004 | Choi | G05D 23/1931 62/180 |
| 2004/0256474 A1 | 12/2004 | Park et al. | |
| 2006/0155421 A1 | 7/2006 | Baek et al. | |
| 2007/0198129 A1 | 8/2007 | Koselka et al. | |
| 2009/0211726 A1 | 8/2009 | Bank et al. | |
| 2010/0043473 A1 | 2/2010 | Koh et al. | |
| 2012/0011873 A1 | 1/2012 | Blackstone et al. | |
| 2012/0096886 A1 | 4/2012 | Palmer et al. | |
| 2013/0029583 A1 | 1/2013 | Zhang et al. | |
| 2013/0036549 A1 | 2/2013 | McKlarney | |
| 2013/0227976 A1 | 9/2013 | Yamashita | |
| 2013/0259456 A1* | 10/2013 | Viswanathan | F24D 13/00 392/407 |
| 2014/0290301 A1 | 10/2014 | Law | |
| 2015/0107295 A1 | 4/2015 | Vreeland et al. | |
| 2015/0135743 A1* | 5/2015 | Dobbs | F24F 11/30 62/115 |
| 2015/0159889 A1 | 6/2015 | Ha et al. | |

FOREIGN PATENT DOCUMENTS

| | | | |
|---|---|---|---|
| GB | 1262011 A | | 2/1972 |
| GB | 2489011 A | | 9/2012 |
| JP | 08-128706 A | | 5/1996 |
| JP | 10259942 A | * | 9/1998 |
| JP | 2004-125376 A | | 4/2004 |
| JP | 2007-079047 A | | 3/2007 |
| WO | WO 2010/137800 A2 | | 12/2010 |
| WO | WO 2013/113513 A2 | | 8/2013 |
| WO | WO 2014/185033 | | 11/2014 |
| WO | WO 2016/033142 A1 | | 3/2016 |

OTHER PUBLICATIONS

Extended European Search Report, dated Apr. 4, 2019, in European Application No. 16808486.1.
Office Action, dated Dec. 14, 2018, in European Patent Application No. 16808486.1.
International Search Report and Written Opinion, dated Nov. 29, 2016, for International Application No. PCT/US2016/037103.
Owano, N. "Throw-and-go Lily captures actions, to ship February," Tech Xplore [online], May 2015 [retrieved Sep. 7, 2017]. Retrieved from the Internet: <URL: https://techxplore.com/news/2015-05-throw-and-go-lily-captures-actions-ship.html>.
U.S. Department of Energy, Advanced Research Projects Agency—Energy, "Robotic Personal Conditioning Device" [online]. Dec. 16, 2014 [retrieved on Dec. 11, 2017]. Retrieved from the Internet: <URL: https://arpa-e.energy.gov/?q=slick-sheet-project/robotic-personal-conditioning-device>.
Notice of Reasons for Refusal, dated Jul. 28, 2020, in Japanese Patent Application No. 2017-564415.

* cited by examiner

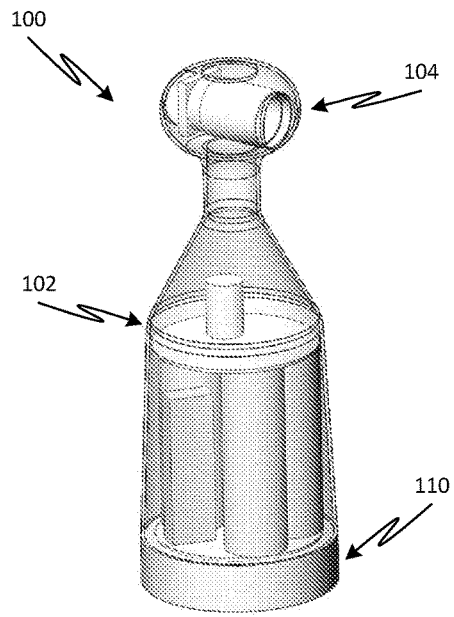 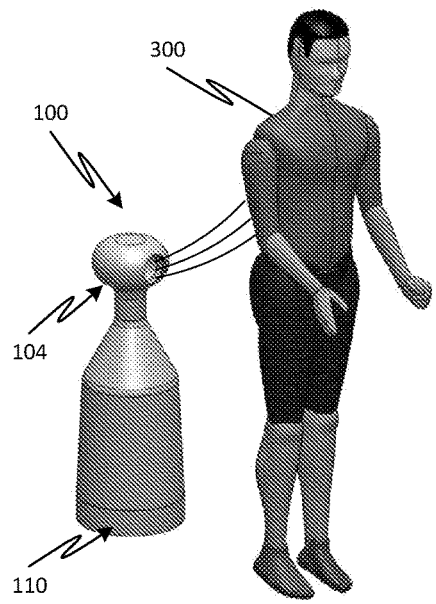
FIG. 3A  FIG. 3B
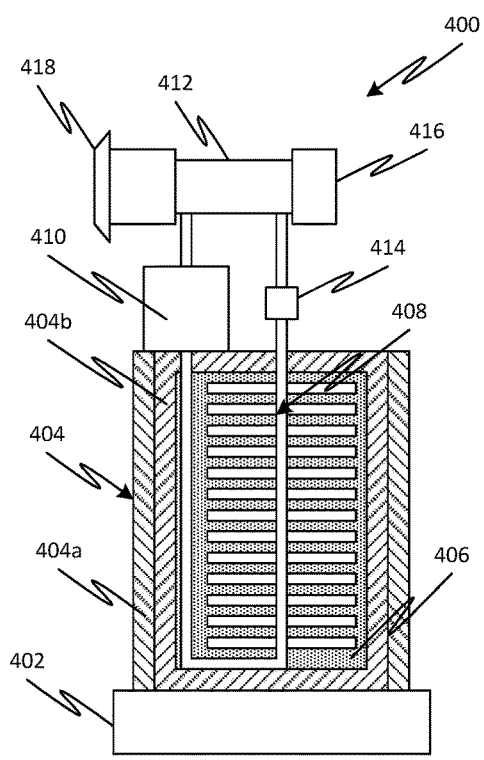 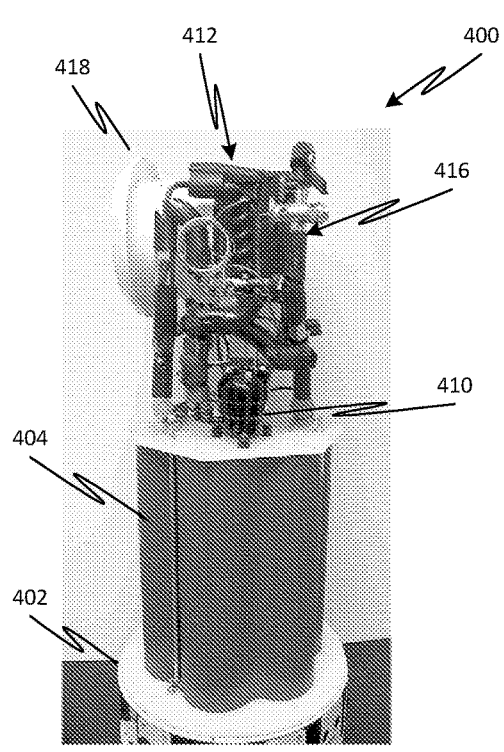
FIG. 4A  FIG. 4B

COMFORT UNITS AND SYSTEMS, METHODS, AND DEVICES FOR USE THEREOF

CROSS-REFERENCE TO RELATED APPLICATIONS

The present application claims the benefit of U.S. Provisional Application No. 62/174,703, filed Jun. 12, 2015, U.S. Provisional Application No. 62/312,302, filed Mar. 23, 2016, and U.S. Provisional Application No. 62/312,310, filed Mar. 23, 2016, all of which are hereby incorporated by reference herein in their entireties.

STATEMENT REGARDING FEDERALLY SPONSORED RESEARCH

This invention was made with government support under DEAR0000530 awarded by Department of Energy (DOE), Advanced Research Projects Agency-Energy (ARPA-E). The government has certain rights in the invention.

FIELD

The present disclosure relates generally to environmental control, and more particularly, to creating a custom comfortable microenvironment for one or more users in an otherwise uncomfortable environment using a comfort unit.

SUMMARY

Embodiments of the disclosed subject matter can provide a customizable microenvironment around one or more users to maintain a comfortable temperature and/or humidity level despite otherwise uncomfortable conditions in the surrounding macro-environment. For example, the surrounding macro-environment may be an office building where conditions are out of the comfortable range to save on energy or for other reasons, a factory/shop environment that is poorly conditioned, or an outdoor location with little to no conditioning. In embodiments, the comfort unit can be configured to follow the user as the user moves within the macro-environment, or to otherwise move within the macro-environment to achieve certain functions, for example, to provide spatial shifting of thermal load within the overall macro-environment.

In one or more embodiments, an environmental control system comprises a comfort unit constructed to create a thermal microenvironment around one or more users. The thermal microenvironment has a temperature different from that of an environment surrounding the microenvironment. The comfort unit can include a thermal regulation module and an air delivery module. The thermal regulation module heats or cools air for the thermal microenvironment, while the air delivery module directs the heated or cooled air to the one or more users to create the thermal microenvironment. The thermal regulation module can include a heat exchanger and a thermal storage material (TSM) thermally coupled to the heat exchanger. The TSM can be constructed to store heat therein.

In one or more embodiments, an environmental control system comprises a multi-function comfort unit constructed to create a thermal microenvironment around one or more users in a first mode of operation and to dehumidify air in a vicinity of the one or more users in a second mode of operation. The thermal microenvironment has a temperature different from that of an environment surrounding the microenvironment. The comfort unit can include a thermal regulation module, an air delivery module, and a condensation tank. The thermal regulation module heats, cools, or dehumidifies air based on the mode of operation. The air delivery module directs the heated or cooled air to the one or more users to create the thermal microenvironment during the first mode of operation. The condensation tank collects water extracted from the air during the second mode of operation. The thermal regulation module can include a heat exchanger and an TSM thermally coupled to the heat exchanger. The TSM is constructed to store heat therein.

In one or more embodiments, an environmental control method comprises detecting a comfort level of one or more users in an environment having a first temperature, and, based on the detected comfort level, generating a microenvironment around the one or more users using a comfort unit. The microenvironment has at least one of temperature and humidity different from that of the environment. The comfort level of at least one user can be improved by the generated microenvironment.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIG. 3A is a three-dimensional model of an exemplary configuration of the comfort unit, according to one or more embodiments of the disclosed subject matter.

FIG. 3B illustrates an exemplary use of a comfort unit by a moving user, according to one or more embodiments of the disclosed subject matter.

FIG. 4A shows a comfort unit having a vapor compression system, where the condenser is embedded in a phase change material (PCM), according to one or more embodiments of the disclosed subject matter.

FIG. 4B is a photograph of a prototype for the comfort unit of FIG. 4A.

DETAILED DESCRIPTION

As disclosed herein, a comfort unit can provide customizable individualized conditioning of air to a user (or multiple users, either simultaneously or sequentially) to create a comfortable microenvironment in an otherwise uncomfortable overall environment. Such environments can include but are not limited to interior spaces of buildings that are maintained at a temperature outside of a comfortable range that can provide overall energy savings or for other reasons. Other environments can include but are not limited to interiors of buildings that have inadequate conditioning systems, outdoor locations that have little or no conditioning, or vehicles that may have little or no conditioning. Thus, the comfort unit may work independently as a substitute for traditional building or vehicle air conditioning systems, or it may work cooperatively with existing building or vehicle air conditioning systems that can operate at an otherwise reduced energy consumption level (i.e., an extended temperature setting) while maintaining comfort of individual users. In such an extended temperature setting, energy savings using the comfort unit can be at least 15%, for example, between 15% and 34%.

In embodiments, the comfort unit can be responsive to the individual comfort of the user, as determined based on inputs from one or more sensors, although in some configurations the comfort unit may work without sensor inputs, for example, in an on-off operation to maintain a set temperature previously determined to be comfortable for the user. The comfort unit can determine when a user is uncomfortable and the degree of the discomfort based on the sensor inputs and can provide conditioned air (heated, cooled, and/or dehumidified) to the user on demand to alleviate the discomfort. To determine the degree of comfort of the user, the system take into account biometric and/or environmental parameters. Within the overall environment, the comfort unit creates around the user a microenvironment of comfortable air that is customized to that user.

In some embodiments, as the user moves through the environment the comfort unit may track and follow the user, so as to keep the microenvironment substantially around the user despite the movement. In some embodiments, the comfort unit can move through the environment to achieve other goals, such as recharging itself, spatially shifting thermal loads, following a predetermined path within the environment, and/or changing modes of operation. In such configurations, the comfort unit may be known as a roving comforter (RoCo) and may be fully or partially autonomous.

Figure 1:
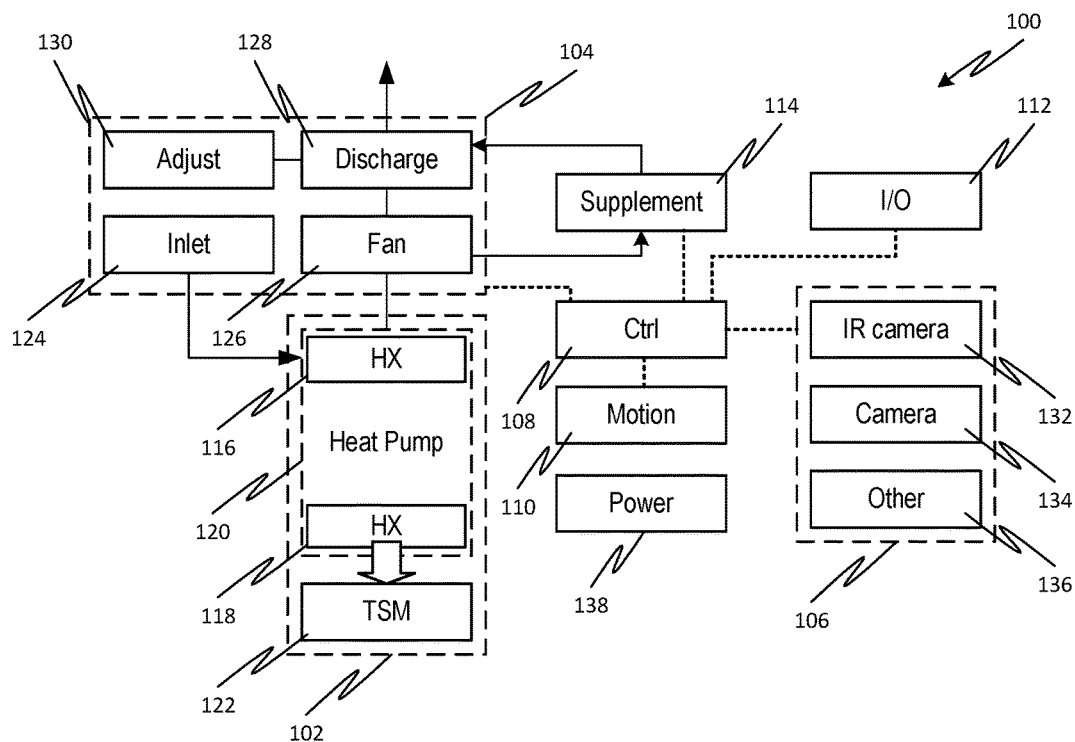
FIG. 1 shows various components of a comfort unit, according to one or more embodiments of the disclosed subject matter.

Referring to FIG. 1, a simplified schematic diagram of a comfort unit 100 according to embodiments of the disclosed subject matter is shown. The comfort unit 100 can include thermal regulation module 102, air delivery module 104, and a sensing module 106, among other components. The thermal regulation module 102 can heat or cool air from the environment, depending on the mode of operation. The air delivery module 104 can direct the conditioned air from the thermal regulation module 102 at the user to create the desired microenvironment. The thermal regulation module 102 can include a heat pump 120 and a thermal storage material (TSM) 122. The TSM 122 can be constructed to store heat therein. As described in more detail below, TSM 122 can be a sensible material or a phase change material (PCM). For example, the sensible material can be heated or cooled water, ice water, a solid or liquid metal, antifreeze, water-glycol mixture, oils, or any secondary working fluid known in the art.

For example, the PCM can be paraffin, salt hydrate, fatty acid, water, or any combination thereof. Alternatively or additionally, the PCM can be constructed to change phase based on application of an external signal thereto in addition to heat transfer. For example, the external signal can be a voltage signal, a current signal, and ultrasonic signal, a magnetic signal, or any combination thereof. In some embodiments, the external signal may be used alone or in combination with heat exchange to recharge the PCM by changing its phase.

The heat pump 120 can include a first heat exchanger 116 and a second heat exchanger 118. Heat can thus be exchanged between the heat pump 120 and the TSM 122 via the heat exchanger 118. Heat exchanger 116 can receive air from the environment to exchange heat therewith. In a heating mode of operation, thermal regulation module 102 can operate to transfer heat stored in the TSM 122 to the air flowing through heat exchanger 116 via heat pump 120. Conversely, in a cooling mode of operation, thermal regulation module 102 can operate to transfer heat from air flowing through heat exchanger 116 and store it in the TSM 122 via heat pump 120. For example, heat pump 120 can be configured as a vapor compression system. However, other types of heat pumps are also possible, such as, but not limited to, a thermoelastic module, a thermoelectric cooler/module and magneto-caloric systems. In some embodiments, the heat pump may be replaced by a simple heat exchanger capable of transferring heat between the TSM 122 and air flowing therethrough, for example, as described with respect to FIG. 4E below.

The cooling capacity of the thermal regulation module 102 can be around 10 to 500 W, or around 10 W to 3 kW per user when multiple users are serviced by the same comfort unit. The heating capacity of the thermal regulation module 102 can be up to 500 W, or about 200 W per user when multiple users are serviced by the same comfort unit. In an extended temperature configuration where an air-conditioning system maintains the environment, the heating/cooling capacity of the thermal regulation module 102 may be substantially less, for example, on the order of 10-20 W.

The air delivery module 104 can include an air inlet 124, a fan 126, and the air outlet or discharge 128. Air from the environment can be sucked into the inlet 124 and passed through the first heat exchanger 116, where the air can exchange heat with the heat pump 120, by action of the fan 126. The resulting conditioned air can be directed by fan 126 to the air outlet 128, for it is directed at the user to create the desired microenvironment. Although shown in a draw-through configuration, embodiments of the disclosed subject matter are not limited thereto. Rather, the fan 126 can be arranged on the other side of the heat exchanger 116, i.e., in a blow-through configuration, as illustrated in, for example, FIG. 4A. The air inlet 124 can be, for example, one or more of a register, a nozzle, a slot, or any other type of air inlet known in the art. The air outlet 128 can be, for example, one or more of a register, a nozzle, a slot, a diffuser, or any other type of air outlet known in the art. The fan 126 can employ, for example, a brushless DC motor.

The air delivery module 104 can optionally include an adjustment mechanism 130 for the air discharge 128. The adjustment mechanism 130 can allow for passive (user manipulation) or active (on board motion control) manipulation of the direction of outlet airflow from the air discharge 128. For example, the air discharge 128 is a single nozzle or an array of nozzles constructed to deliver as much effective cooling/heating as possible to a user at a minimum energy consumption and to body parts of the user in need of cooling/heating. The air discharge 128 thus directs conditioned air toward selected parts of the user's body to produce optimal effect and thermal sensation. The adjustment mechanism 130 can allow the air discharge 128 to move in at least one dimension, preferably in three dimensions, in order to direct the airflow to achieve these goals. For example, in cooling mode, the outlet air may be directed at the head or upper torso of the user, while in a heating mode the outlet air may be directed at the feet or lower extremities of the user. Alternatively or additionally, the user may manipulate the air discharge 128 via the adjustment mechanism 130 to direct the airflow at a desired body part, for example, to heat up cold hands. In such configurations, the adjustment mechanism 130 may comprise a telescoping portion that allows the height of the outlet and/or a location of the outlet with respect to a body of the comfort unit to be changed, either by the user or by the control module 108.

The comfort unit 100 can also have a sensing module 106, which can include an IR camera 132 and/or a visible light camera 134. The sensing module 106 can also include one or more additional optional sensors 136, for example, sensors that measure biometric data and/or environmental data, sensors for navigation control of the comfort unit 100, sensors for security monitoring of the environment, and/or sensors for motion control (e.g., gyro, acceleration, tilt, altitude, etc.). The IR camera 132 can be used to image the user order to measure a clothing level or other thermal insulation of the user, which data can be used in determining the comfort level of the user. The visible light camera 134 can be used by the comfort unit 100 navigating through the environment, for example, to detect obstacles in its path. Alternatively or additionally, the visible light camera 134 can be used to image the user, whereby facial recognition processing of the image of the user can be used by the comfort unit 100 to determine user and its preferences. Alternatively or additionally, the IR camera 132 and/or the visible light camera 134 may be used to image the user during generation of the thermal microenvironment to provide feedback regarding personal thermal sensation of the user.

Moreover, the facial recognition processing can be used by the comfort unit 100 to track the user within the environment and to follow the user. Alternatively or additionally, the sensing module 106 can include sensors that detect the location of the user and/or obstacles within the environment. For example, the sensing module 106 can employ directional wireless signals, directional radio frequency (RF) signals, and/or Bluetooth low energy beacons. Alternatively or additionally, the user can have a communication device, such as a smart phone or a wearable, that is detected and tracked by the sensing module 106.

The comfort unit 100 can also include a control module 108, which controls various aspects and operation of the comfort unit 100. Thus, the control module 108 can be operatively connected to the thermal regulation module 102, the air delivery module 104, and the sensing module 106 to receive signals therefrom and send control signals thereto. In particular, the control module 108 can control the thermal regulation module 102 and/or the air delivery module 104 responsively to a signal indicative of a comfort level of the user. Thus, when the user is uncomfortable as indicated by the signal, the control module 108 directs the thermal regulation module 102 and/or the air delivery module 104 to generate a thermal microenvironment around the user based on the user's preferences (which may have been previously input to the comfort unit 100 or may be autonomously determined based on sensing of biometric data of the user) to make the user comfortable.

The comfort unit 100 can also include additional modules, such as an optional motion control module 110, a power supply 138, an optional supplemental module 114, and an input/output (I/O) module 112, which are operatively connected to the control module 108. The motion control module 110 moves the comfort unit 100 within the environment. The motion control module 110 can support the other modules of the comfort unit 100 thereon, and can include any combination of motors, gears, wheels, etc. to effect the desired motion. The motion control module 110 can be operatively connected to and receive commands from the control module 108, which may direct the motion control module 110 to, for example, track the user, to move along a predetermined path within the environment, or to dynamically move to a location within the environment to perform a desired operation (e.g., recharging or thermal load shifting). The motion control module 110 may be considered a robotic platform.

Since the comfort unit 100 is constructed to operate independently of the environment, it is provided with onboard power supply 138. The power supply 138 is connected to each of the other modules of the comfort unit 100 (connections not shown for clarity) to power operation thereof. For example, the power supply 138 can be a rechargeable battery, such as lithium-ion battery, zinc-ion battery, lithium-polymer battery, deep cycle lead-acid battery, and zinc-air battery. In another example, the power supply 138 is a removable battery that can be replaced by a user upon depletion. The rechargeable or removable battery may be formed as a non-regular shape, for example, via 3-D printing for easy integration or replacement. Alternatively or additionally, the power supply 138 can comprise a wireless power converter for turning wirelessly transmitted energy (e.g., in a floor over which the comfort unit 100 sits) into useable power. Such wireless power transmission systems can be configured as inductive or resonant systems, or in any configuration known in the art.

The I/O module 112 can provide a communications link between the control module 108 and an external device (e.g., sensing unit 200, other comfort units 100, or a central control unit 602, described in further detail below). The communications link may be a wireless communication link, for example, via a Wi-Fi network, a cellular network, Bluetooth communication, ZigBee, ZWave, or any other wireless communication protocol known in the art. Alternatively or additionally, I/O module 112 can enable communication between the control module 108 and the user. For example, the I/O module 112 can include an on-device user interface by which the user can interact with the comfort unit 100 to set desired preferences or other requirements. Alternatively or additionally, the user interface may be located separate from the body of the comfort unit 100, for example on a sensing unit 200, and may communicate with the comfort unit 100 via the I/O module 112.

The supplemental module 114 can provide one or more secondary functions separate from, or complementing, the thermal regulation module 102 and the air delivery module 104. For example, the secondary functions may include additional processing of the air prior to or after conditioning by the thermal regulation module 102. Such secondary functions can include, but are not limited to, air purification, air ionization, humidification, and dehumidification. Alternatively or additionally, the secondary functions offered by the supplemental module 114 can be unrelated to the processing of the air, for example, by providing a storage compartment for items to be transported by the comfort unit 100 and used by the user or by processing and providing alerts based on the security monitoring by the sensing module 106.

Figure 2:
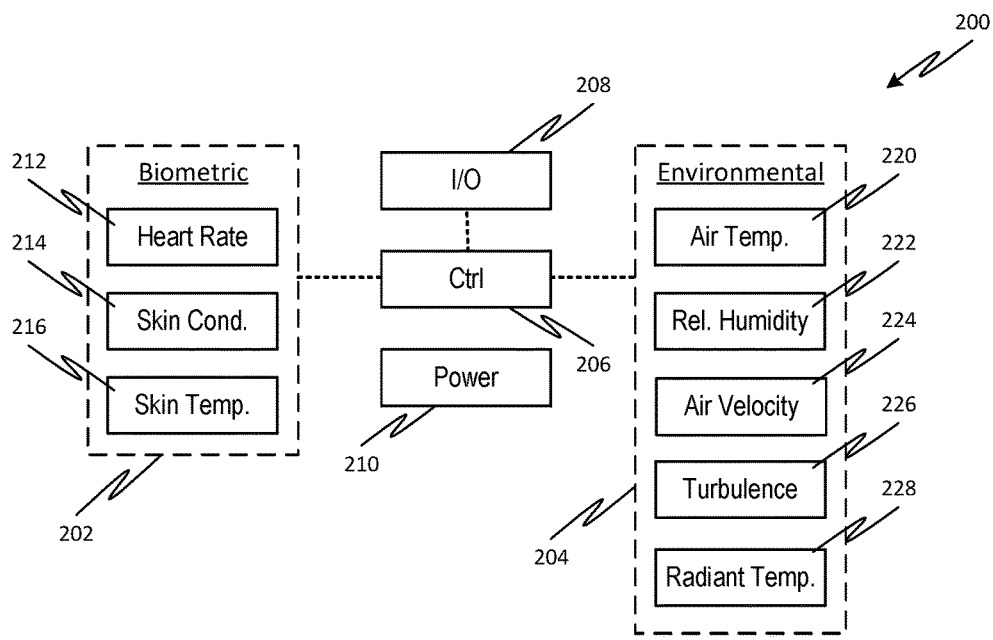
FIG. 2 shows various components of a sensing unit, according to one or more embodiments of the disclosed subject matter.

Referring to FIG. 2, a simplified schematic diagram of a sensing unit 200 according to embodiments of the disclosed subject matter is shown. The sensing unit 200 can monitor a user (or users) in the environment for comfort level and can work cooperatively with the comfort unit 100 to condition air to improve the comfort level of the user. The sensing unit 200 can include a biometric data sensing module 202, an environmental data sensing module 204, and a data processor or control module 206. As with the comfort unit 100, the sensing unit can include its own power supply 210, which may be a removable or rechargeable battery, or a wireless power converter. The sensing unit 200 can also include an I/O module 208, which can include wireless communication components or an on-device user interface, similar to the I/O module 112 of the comfort unit 100 described above.

The biometric data sensing module 202 can include one or more sensors that measure heart rate 212, skin conductance 214, and/or skin temperature 216. The data processor module 206 can determine a metric indicative of the comfort level of the user based on at least the detected biometric data. For example, the data processor module 206 can determine a ratio of low spectral frequency (LF) heart rate variability to high spectral frequency (HF) heart rate variability. Thus, the heart rate sensor 212 should have an accuracy sufficient to differentiate between the LF band (i.e., 0.04-0.15 Hz) and the HF band (i.e., 0.15-0.40 Hz). A higher ratio of LF to HF corresponds to a higher level of discomfort for the user. Combining the LF/HF ratio with other measurements can yield a more definitive picture of the comfort level of the user.

For example, the skin conductance can be measured as the galvanic skin response reflecting the change in electrical properties of the skin associated with the evaporative transfer from the user's skin. The skin temperature can be used to quantify the heat transfer between the user and the environment. Each of the skin conductance and the skin temperature measurements can be compared to respective predefined ranges indicative of a particular user's, or a generalized user's, preference. For example, the predefined ranges might be established based on feedback from the user during a setup of the comfort unit system or by manual intervention by the user during normal operation, or by any other means. Based on the LF/HF ratio and the comparison of conductance and temperature with the predefined ranges, the system can estimate a comfort level of the user. Alternatively or additionally, the heart rate, conductance, and temperature measurements can be combined into a metric indicative of comfort level.

As noted above, the comfort unit 100 may include an IR camera that can image the user. Analysis of the IR image can provide an estimate of clothing level by comparing the temperature of the outer most layer of clothing to the temperature measured by skin temperature sensor 216. The determined clothing level can add a resistance factor in an overall heat transfer calculation between the user and the environment. This data can be transferred to the sensing unit 200 for processing by processor 206 via I/O module 208. Alternatively or additionally, the data from the sensing unit 200 can be transferred to the comfort unit 100 or to a separate control unit (e.g., control unit 602 in FIG. 6A) for processing and determination of comfort level.

Figure 5A:
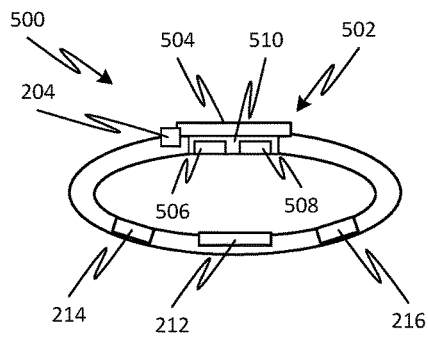
FIG. 5A shows a sensing unit that is wearable on a user's wrist, according to one or more embodiments of the disclosed subject matter.
Figure 5B:
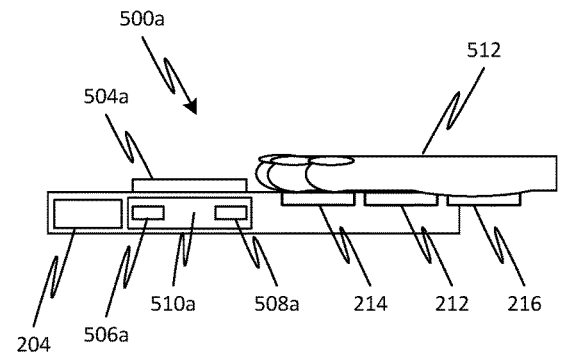
FIG. 5B shows a standalone sensing unit for periodic contact with the user, according to one or more embodiments of the disclosed subject matter.
Figure 5C:
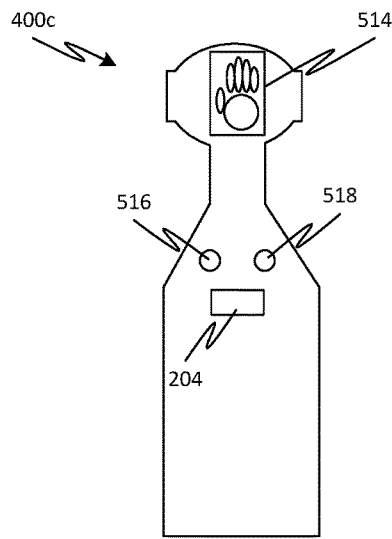
FIG. 5C shows a comfort unit including aspects of the sensing unit, according to one or more embodiments of the disclosed subject matter.

To obtain the biometric data, the sensors of the biometric data sensing module 204 may be in direct contact with the skin of the user. For example, the sensing unit 200, or portions thereof, can be a wearable device, such as a watch, bracelet, necklace, chest strap, shoe insert, underwear garment, or arm band. In another example, the sensing unit 200, or portions thereof, can be a standalone device that a user intermittently touches, for example, to turn conditioning by the comfort unit on. In still another example, the sensing unit 200, or portions thereof, can be integrated with the comfort unit 100. Such examples are illustrated in FIGS. 5A-5C and discussed in more detail below. However, the sensing device 200 may also be embodied as any combination of the above described examples, for example, as a wearable device for the biometric data sensing module 202 and as a standalone device for the environmental data sensing module 204.

Other configurations are also possible according to one or more contemplated embodiments.

The environmental data sensing module 204 can include one or more sensors that measure various characteristics of the environment or microenvironment, such as air temperature 220, relative humidity 222, air velocity 224, turbulence 226, and radiant temperature 228. Other sensors are also possible, such as, but not limited to, air quality and $CO_2$ sensors. Although indicated as separate items, it is contemplated that a single sensor of the environmental data sensing module 204 can measure more than one variable. For example, an omnidirectional anemometer can be used to measure air velocity 224 as well as turbulence intensity 226. In another example, the radiant temperature 228 may be determined based on data from the IR camera 132 of the comfort unit 100, or by using a separate sensor, such as a glob thermometer. For example, the temperature sensors (both biometric and environmental) can have an accuracy of ±0.5° C., and the humidity sensor can have an accuracy of 2-5%.

Together with the biometric data, the environmental data can be used to infer a comfort state of the user and control the comfort unit 100 to provide desired conditioning to increase the user's comfort. For example, the processor 206 can process data from the biometric data module 202 and the environmental data module 204 and compare each data point to respective predefined ranges indicative of comfort to determine the user's comfort level. Based on the comparison, the processor 206 can determine if the user is cold, hot, or neutral based on the user's preferences. When the comparison indicates discomfort (e.g., a cold or hot state), a signal can be sent to the comfort unit 100 that causes it to automatically adjust the position of air delivery, the air speed, thermal capacity, and/or conditioning mode (e.g., heating or cooling) until the user reaches a neutral state.

Examples of a comfort unit are illustrated in FIGS. 3A-4F and 9A-9D, while examples of a sensing unit are illustrated in FIGS. 5A-5C. FIGS. 3A-3B show a three-dimensional model of a mobile comfort unit 100 having a thermal regulation module 102 and an air delivery module 104 supported on a motion control module 110 (e.g., a robotic platform) that can move the comfort unit 100 to follow a user 300. The microenvironment generated by air from air delivery module 104 can thus move with the user 300 to keep the user comfortable with the environment, as shown in FIG. 3B. The comfort unit 100 illustrated in FIGS. 3A-3B can have be around 1 m tall (e.g., about 900 mm) and around 0.5 m in width (e.g., about 400 mm in diameter).

FIG. 4A shows a simplified cross-sectional side view of a comfort unit 400 that uses a vapor compression system for the heat pump in the thermal regulation module. FIG. 4B is a photograph of a prototype of the comfort unit 400 similar to the arrangement shown in FIG. 4A. The comfort unit 400 includes a platform 402, which may be a motion control module (e.g., robotic platform) as described above, or a stationary platform. The platform 402 can support some components of the comfort unit 400, or all of the components of the comfort unit 400, as illustrated in FIG. 4A. A container 404 that houses the TSM 406 can be mounted on the platform 402.

The vapor compression system includes a first heat exchanger 408, a compressor 410, a second heat exchanger 412, and an expansion valve 414 connected together in a loop. Refrigerant flowing through the loop is used to transfer heat between the first heat exchanger 408 and the second heat exchanger 412. A fan 416 can blow air from the environment through the second heat exchanger 412 for heat transfer. The resulting conditioned air can be exhausted to the environment through one or more nozzles 418. The first heat exchanger 408, for example a tube and fin heat exchanger, can be surrounded by the TSM 406 within container 404 such that heat can be transferred between the heat exchanger 408 and the TSM 406. Alternatively, the first heat exchanger 408 can have one or more tubes disposed within the TSM 406, each to having a diameter less than 2 mm. For example, the first heat exchanger can be a microchannel heat exchanger.

When the comfort unit 400 operates in a cooling mode, heat from the air directed by fan 416 is absorbed by the second heat exchanger 412 (i.e., the evaporator) and transferred to the first heat exchanger 408 (i.e., the condenser), where the heat is stored in the TSM. As a result, the air exiting nozzle 418 has been cooled. The storage in the TSM 406 of the waste heat from heat exchanger 408 prevents this heat from being exhausted to the environment surrounding the user, which would otherwise be required if the TSM storage were not available. As a result, the building load will not be increased. The absorbed heat can be released at a later time (time-shifting) or at a different location (space-shifting) to avoid increasing building load and/or disrupting user comfort. For example, the TSM can release the stored heat at night or at a location where building load does not matter (e.g., outside or in a zone of the building that is otherwise over-conditioned). Alternatively or additionally, a different energy source can be used to recharge the TSM 406, as described in further detail below.

The comfort unit 400 can have a switch (not shown) that reverses the vapor compression system to operate in a heating mode. When the comfort unit 400 operates in the heating mode, heat stored in the TSM 406 is transferred from the first heat exchanger 408 (now operating as the evaporator) to the second heat exchanger 412 (now operating as the condenser), where the heat is absorbed by the air directed by fan 416. As a result, the air exiting nozzle 418 has been heated.

In some embodiments, the TSM 406 is a phase change material (PCM) that stores or releases heat by undergoing a change in phase. Examples of appropriate PCM materials include, but are not limited to, paraffin, salt hydrate, fatty acid, water, and combinations thereof. The PCM may have a melting temperature slightly above standard room temperature, so that it may be melted by heat transfer during the cooling mode and solidified by heat transfer during the heating mode.

In some embodiments, the container 404 can have multiple separate layers between the TSM 406 and the external environment of the comfort unit 400. For example, the container 404 can have an outer layer 404a and an inner layer 404b. The outer layer 404a may have a different insulation property (e.g., different insulating factor) from that of the inner layer 404b. Alternatively, the outer layer 404a may have the same insulation properties as that of the inner layer 404b, but may have other characteristics that are different from the inner layer 404b, for example, a different thickness. In still another alternative, the outer layer 404a may be substantially identical to the inner layer 404b. The outer layer 404a can be removable from the inner layer 404b, so that the insulating properties of the container 404 can be changed, for example, to allow more heat to transfer between the TSM and the external environment. Alternatively or additionally, the inner layer 404b may also be removable to increase the amount of heat transfer between the TSM material and the external environment.

Figure 4C:
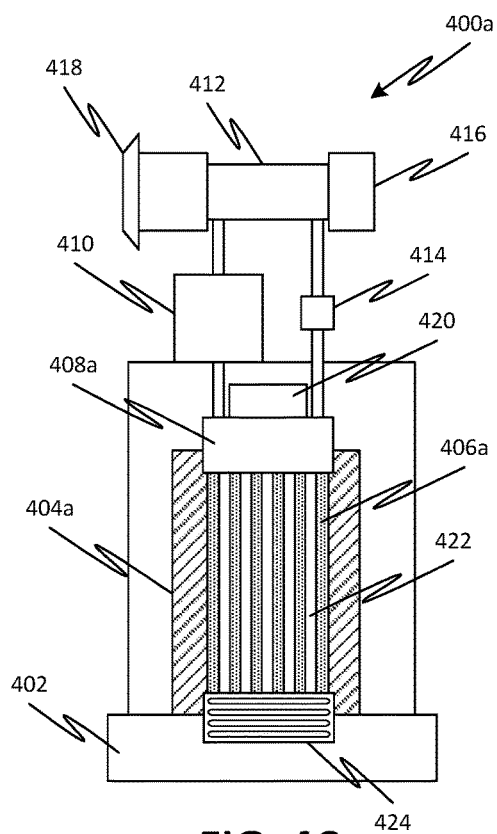
FIG. 4C shows another comfort unit having a vapor compression system, where the PCM receives air from the condenser, according to one or more embodiments of the disclosed subject matter.
Figure 4D:
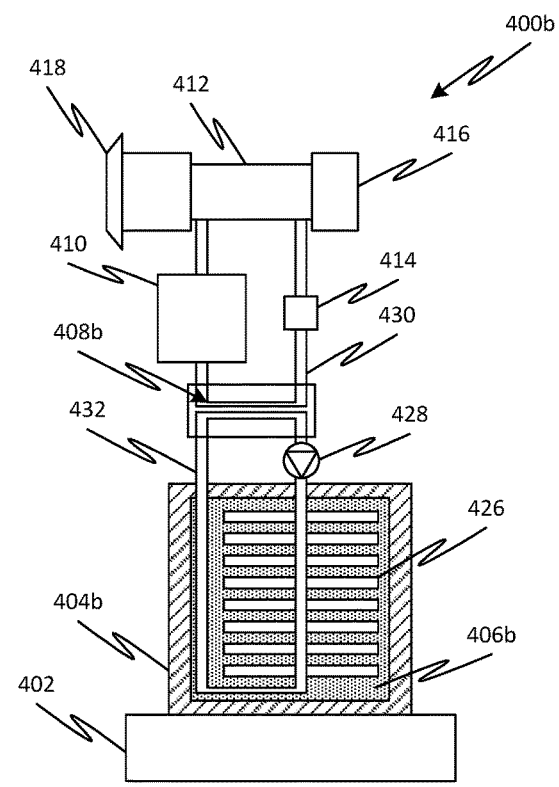
FIG. 4D shows another comfort unit having a vapor compression system, where the PCM is coupled via a separate fluid loop, according to one or more embodiments of the disclosed subject matter.

Although a particular configuration for the thermal regulation module of the comfort unit has been illustrated in FIGS. 4A-4B, other configurations are also possible according to one or more contemplated embodiments. For example, FIG. 4C shows a simplified cross-sectional view of a comfort unit 400a that uses a vapor compression system with air flowing through the TSM 406a. Some features of comfort unit 400a are similar to those of the comfort unit 400 of FIG. 4A. Accordingly, only those features that are different from FIG. 4A will be discussed below.

In FIG. 4A, the first heat exchanger 408 was embedded in the TSM 406, and heat transfer occurred between the refrigerant in the heat exchanger 408 and the TSM 406. In contrast, the comfort unit 400a of FIG. 4B includes a first heat exchanger 408a coupled to a fan 420 such that air directed by fan 420 undergoes heat transfer with the refrigerant flowing through the first heat exchanger 408a. The air can then flow through the TSM 406a, for example, via one or more air flow channels in the TSM 406a, for heat transfer therewith. After flowing through the TSM 406a, the conditioned air can then be exhausted to the environment, for example, via vent 424.

Although shown as separate components, fan 416 and fan 420 may in fact be the same fan, with different air paths from a single fan leading to different heat exchangers. Alternatively or additionally, one of the air paths may be blocked off (e.g., by a valve) such that air flow is directed primarily to one of the heat exchangers. For example, the air flow path through heat exchanger 412 may be blocked off such that air flows only to heat exchanger 408a to enable recharging of the TSM 406a using air from the environment.

In FIG. 4C, a simplified cross-sectional view of a comfort unit 400b that uses a vapor compression system coupled to the TSM 406b via an independent fluid loop is shown. Some features of comfort unit 400a are similar to those of comfort unit 400 of FIG. 4A. Accordingly, only those features that are different from FIG. 4A will be discussed below.

As noted above, in FIG. 4A, the first heat exchanger 408 was embedded in the TSM 406, and the transfer occurred between refrigerant in the heat exchanger 408 and the TSM 406. In contrast, the comfort unit 400b of FIG. 4C includes a first heat exchanger 408b through which a first fluid loop 430 and a second fluid loop 432 are disposed in thermal communication with each other. A pump 428 moves fluid through the second fluid loop 432 between the heat exchanger 408b and the TSM 406b. Thus, heat can be transferred from the first fluid loop 432 the TSM 406b via the second fluid loop 432.

Figure 4E:
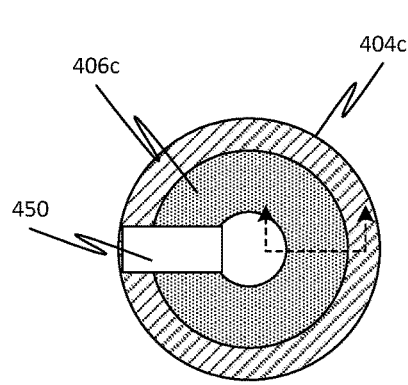
FIG. 4E is a simplified top view of a PCM-heat exchanger assembly, where the PCM is a three-dimensional porous matrix, according to one or more embodiments of the disclosed subject matter.
Figure 4F:
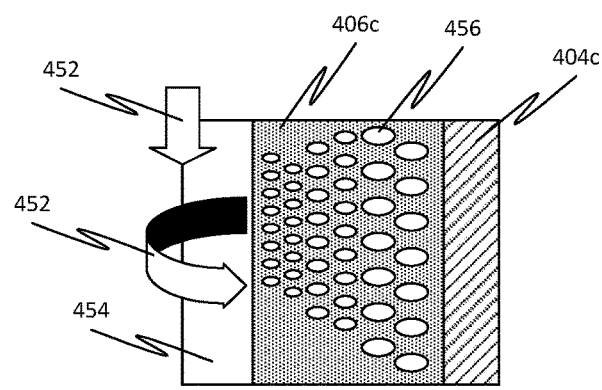
FIG. 4F is a partial cross-sectional view of the PCM-heat exchanger assembly of FIG. 4E.

In an alternative configuration, the TSM can be constructed as a three-dimensional porous structure or matrix (e.g., like a sponge). Air can thus flow through the TSM via the network of connected pores therein in order to enable heat transfer between the flowing air and the TSM. In such configurations, the TSM may be a phase change material (PCM), which would thus lose its structure upon melting. Such a configuration is illustrated in FIGS. 4E-4F. For example, the PCM 406c disposed in container 404c can have a network of pores 456 distributed throughout. A fan/heat exchanger assembly 450 can be coupled to a top of the container 404c for directing an air flow 452 along a central flow channel 454 in the container. Air in the flow channel 452 can flow into the PCM 406c via the pores for the desired heat exchange. A separate exhaust channel (not shown) may be provided to conduct air from the PCM 406c to outside the container 404c and/or the comfort unit.

In another configuration (not illustrated) the thermal regulation module operating in a vapor compression cycle is constructed as a single rotating assembly. The compressor can be a hermetic compressor mounted such that, when the compressor motor is energized, the entire hermetic compressor rotates. For example, the compressor shell can be mounted such that it can rotate freely, while the rotor stays stationary or rotates at a considerably slower rate than the stator. In a cooling mode, the compressed refrigerant vapor can be discharged to the condenser, which can include an air moving device (e.g., fan) that rotates with an exterior of the compressor. The compressed refrigerant vapor condenses in flow passages inside the fan blades of the condenser. The liquid refrigerant discharged from the condenser flows through a suitable expansion device to the evaporator, which can include another air moving device (e.g., fan). The refrigerant can evaporate in the blades of the evaporator upon exposure to air from the environment, thereby cooling the air. The compressor, condenser air-moving device, expansion device, and evaporator air-moving device can be part of a single rotating assembly that is hermetically sealed.

Other configurations for effecting heat transfer between the air and the TSM besides those specifically discussed above and elsewhere herein are also possible according to one or more contemplated embodiments. Accordingly, embodiments of the disclosed subject matter are not limited to those configurations explicitly discussed herein.

Referring to FIG. 5A, an embodiment of the sensing unit 500 that is wearable by a user is shown. The sensing unit 500 can be constructed to be worn by the user, for example, on the wrist of the user like a watch or bracelet. As discussed above, the sensing unit 500 can include one or more biometric sensors, such as heart rate sensor 212, skin conductance sensor 214, and skin temperature sensor 216. The sensing unit 500 can also optionally include one or more environmental sensors 204. The biometric sensors may be disposed on the sensing unit 500 so as to make constant or periodic contact with the skin of the user. The one or more environmental sensors 204 may be disposed on the sensing unit 500 away from the user's skin and directed toward the environment generally.

The sensing unit 500 can also include, for example, a multi-function module 502 disposed so as to be viewable by the user. The multi-function module 502 can include, for example, a user interface or display 504, an input/output module 506, a power supply 508, and/or a control module 510. The control module 510 can control operation of the sensing unit 500 including the processing of data signals from the biometric and environmental sensors. The power supply 508 can supply power to the control module 510 as well as the other components of the sensing unit 500. For example, the power supply 508 is a battery. The input/output module 506 can be used to communicate the data signals from the biometric and environmental sensors to the comfort unit or another system control unit. For example, the input/output module 506 can employ wireless or Bluetooth communication. The user wearing the sensing module 500 can interface with it via the display 504, for example, to view values measured by the biometric environmental sensors, to command the comfort unit for manual control, to turn the system on or off, or for any other purpose.

Although a particular configuration for the sensing unit has been illustrated in FIG. 5A, other configurations are also possible according to one or more contemplated embodiments. For example, FIG. 5B shows a simplified side view of another configuration of the sensing unit. In contrast to the wearable sensing unit of FIG. 5A, sensing unit 500a is constructed as a standalone unit for periodic contact with the user. For example, sensing unit 500a may sit on top of the desk that the user works at and that the user can touch at various times to provide an indication of their comfort level. In another example, sensing unit 500a may be attached or otherwise mounted to a wall that the user touches to activate the comfort unit.

As discussed above, the sensing unit 500a can include one or more biometric sensors, such as heart rate sensor 212, skin conductance sensor 214, and skin temperature sensor 216. The sensing unit 500a can also optionally include one or more environmental sensors 204. The biometric sensors may be disposed on the sensing unit 500a such that a user can place their hand 512 or other part of their body and contact therewith. The one or more environmental sensors 204 may be disposed on the sensing unit 500a so as to be directed toward the environment generally, and may be at a position remote from where the user touches.

The sensing unit 500a and also include, for example, a user interface or display 504a, and input/output module 506a, a power supply 508a, and/or a control module 510a. As with the other described embodiment of the sensing unit, the control module 510a can control operation of the sensing unit 500a including the processing of data signals from the biometric and environmental sensors. The power supply 508a can supply power to the control module 510a as well as the other components of the sensing unit 500a. For example, the power supply 508a can be a battery, a converter for wireless power, or a wired connection to the power of the building or other external power supply. The input/output module 506a can be used to communicate the data signals from the biometric and environmental sensors to the comfort unit or another system control unit. For example, the input output module 506 can employ wireless or Bluetooth communication, or a hardwired connection to an internal or external network of the environment.

In yet another configuration for the sensing unit, one or more aspects of the sensing unit are integrated with the comfort unit. FIG. 5C illustrates such an embodiment, where comfort unit 400c includes a touchpad 514 that a user can touch to provide the desired biometric data, e.g., heart rate, skin conductance, and skin temperature. For example, the user may touch the touchpad 514 when the when the user first turns on the comfort unit 400c and intermittently thereafter, perhaps when the user believes the environment is becoming uncomfortable. As noted above, the comfort unit 400c may also include one or more cameras, such as infrared camera 516 and visible light camera 518. Infrared camera 516 may be used to estimate an insulation level provided by a user's clothing, while the visible light camera 518 may be used to identify and/or track user through the environment and/or avoid obstacles in the environment.

Other configurations for sensing of biometric and environmental data besides those specifically discussed above and elsewhere herein are also possible according to one or more contemplated embodiments. Accordingly, embodiments of the disclosed subject matter are not limited to those configurations explicitly discussed herein.

Figure 6A:
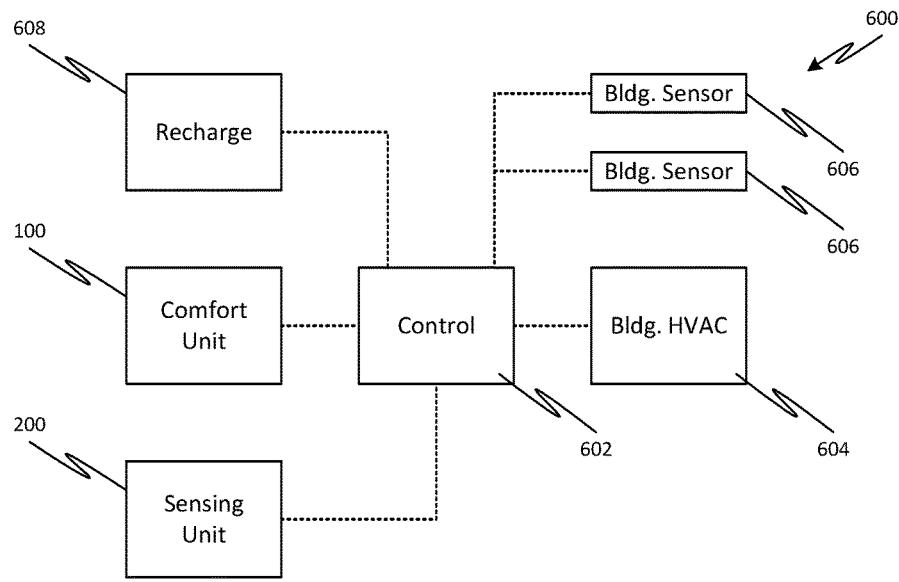
FIG. 6A is a simplified schematic illustrating a configuration of a comfort unit with a building air conditioning system, according to one or more embodiments of the disclosed subject matter.

The comfort unit can be used together with existing building infrastructure, for example, a central air-conditioning unit, to improve the comfort level of the user while reducing overall energy consumption. In this sense, control of the building infrastructure and the comfort unit (or multiple comfort units) can be cooperative to achieve the desired comfort and energy goals. Referring to FIG. 6A, a simplified schematic diagram of an environmental control system 600, incorporating existing building infrastructure and the disclosed comfort unit. Thus, the environmental control system 600 includes a building HVAC system 604, a comfort unit 100, a sensing unit 200, and a central control system 602. The central control system 602 can interface which each of the different elements of the environmental control system 600 to provide the desired control.

The existing building infrastructure can include, besides the building HVAC system 604, one or more building sensors 606 that are used as feedback to control a temperature of the environment using the building HVAC system 604. The comfort unit 100 and the sensing unit 200 can share additional data regarding the environment and/or the comfort level of the user. For example, the comfort unit 100 and/or the sensing unit 200 can communicate with the central control system 602 via a wireless network. Sensory information gathered by the comfort unit and/or the sensing unit can be used for better control of the building HVAC system 604. Moreover, current and/or predictive weather information can also be acquired (e.g., via the Internet) for predictive modeling and control of the building HVAC system 604 and/or the comfort unit 100.

The central control system 602 can employ energy saving algorithms that utilize feedback of user thermal comfort and thereby control both the comfort unit 100 and the building HVAC system 604 to reduce overall energy consumption. For example, this can be achieved by relaxing zone temperature set points of the building HVAC system 604 on a temporary or continual basis. The comfort unit 100 maintains thermal comfort of the user during these periods of relaxation. The central control system 602 can be for example a server that uses application programming interfaces to relax temperature set points at building zone levels toward the balance of thermal comfort. For example, on days where heating is desired, the set points of the building HVAC system 604 can be lowered. Conversely, on days where cooling is desired, the set points of the building HVAC system 604 can be raised.

The central control system 602 can set zone temperatures based on a number of factors and inputs including, but not limited to, time of day, occupancy rate, local weather, current building HVAC settings, feedback regarding thermal comfort of a user, and number and/or capacity of comfort units available for use. Utilizing the comfort units during these energy-saving zone temperature relaxation periods results in a fleet (one or more) of personalized cooling units that can temporarily act to store heat for later thermal management. For example, during these periods of relaxation, the temperature maintained by the HVAC system may be different by at least 4° (higher or lower) than it would otherwise be set to maintain user comfort. The comfort unit 100 may then maintain a microenvironment around the user that has a temperature that is at least 4° different from the environment, thereby maintaining the comfort level of the user despite the otherwise uncomfortable environmental temperature.

Although only a single comfort unit 100 is illustrated in FIG. 6A, multiple comfort units can be used in a single setting according to one or more contemplated embodiments. In such configurations, each comfort unit can be capable of communicating with other comfort units in the vicinity, for example, through wireless networking. For example, the multiple comfort units can act independently, each providing a custom microenvironment for single user or group of users. Alternatively or additionally, the multiple comfort units can work cooperatively to provide a customized microenvironment for one or more users.

Moreover, the environmental control system can include components that enable the desired communication between the comfort unit 100, the sensing unit 200, and/or the central control system 602. For example, communication platform underlying the environmental control system 600 can include on-device sensors, sensors on the user, Bluetooth low energy beacons used to locate the user and/or comfort units within different building zones, and a server communicating with the comfort units. In addition, the communication platform can utilize a control communication service utilizing device and building application program interfaces running on a local or cloud-based server. For example, the control communication service can include a web service to read and write control and building automation system settings and a web service to read and write controls for any number of comfort unit settings. The control and building automation system settings can include, but are not limited to, zone level temperature set points and ventilation rate. The comfort unit settings can include, but are not limited to, fan speed, heating/cooling mode, supply air temperature, location, thermal storage level, thermal storage exhaust, and air distribution control (for devices with multiple nozzles).

Figure 6B:
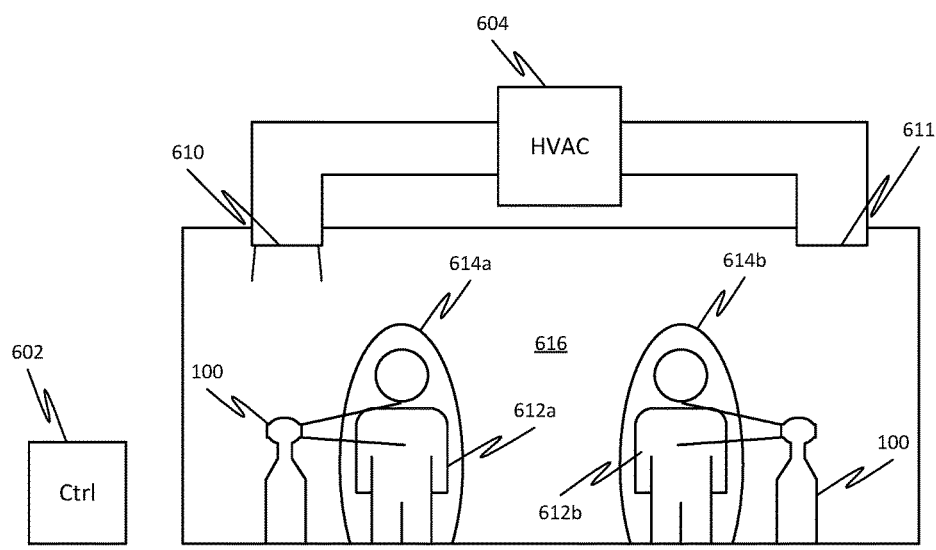
FIG. 6B illustrates the operation of multiple comfort units in a building environment together with a building air conditioning system, according to one or more embodiments of disclosed subject matter.
Figure 6C:
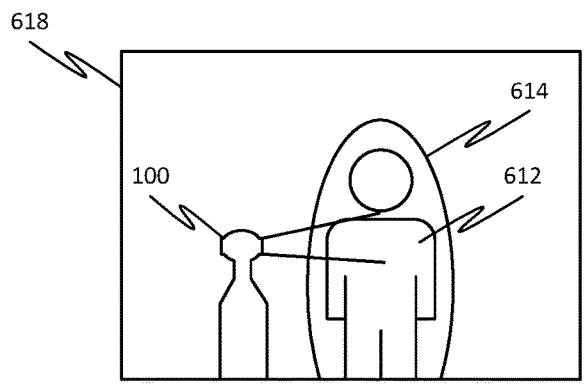
FIG. 6C illustrates the operation of a comfort unit in an independent environment, or without any building air conditioning system, according to one or more embodiments of the disclosed subject matter.

FIG. 6B illustrates the use of multiple comfort units 100 within a building having its own HVAC system. For example, the HVAC system may have an inlet register 611 that takes air in from the environment 616 and an outlet register 610 that directs conditioned air from the HVAC into the environment 616. As shown in the figure, each user 612a, 612b may have a respective comfort unit 100 that creates a customized microenvironment 614a, 614b around the user within the environment 616. The comfort unit 100 may operate in a similar manner in an environment 618 where a building HVAC system is not available, for example, in a building or vehicle that lacks an HVAC system, or outdoors, as illustrated schematically in FIG. 6C.

Although the discussion above focuses on the use of the comfort unit by a single user, embodiments of the disclosed subject matter are not limited thereto. Indeed, it is contemplated that a comfort unit can be used by multiple users to experience a more comfortable microenvironment within the overall uncomfortable environment. For example, the comfort unit can have multiple nozzles to direct air at multiple users at the same time. In such a configuration, the directed air stream for each user can be customized (e.g., different temperatures and/or humidity levels) to allow each user to have their own microenvironment. In other configurations, the directed air stream for each user is substantially the same and can generate a common microenvironment for all of the users. In another example, the comfort unit can move the nozzle (e.g., oscillating or swinging) or itself (e.g., moving along a predefined path) to sequentially and separately direct air at each user.

Although the discussion above focuses on the use of a single comfort unit, embodiments of the disclosed subject matter are not limited thereto. Rather, multiple comfort units may be used simultaneously to create a combined microenvironment or a separate microenvironment according to one or more contemplated embodiments. For example, a single user can be serviced by multiple comfort units, with different temperature air streams directed at different parts of the body. In another example, multiple users can be serviced by multiple comfort units, for example, during a conference or a meeting.

Thermal storage management of the comfort units 100 can provide another method of energy savings in addition to the reduced energy consumption during the relaxation periods. The thermal storage can be managed by the central control system, for example, using the web service application programming interfaces detailed above. Thermal storage management of the comfort unit can be handled in one of two ways. First, thermal loads can be time shifted. In this scenario, the central control system coordinates one or more of the comfort units to vent their thermal capacity into the building or outdoor environment during unoccupied periods.

Figure 7:
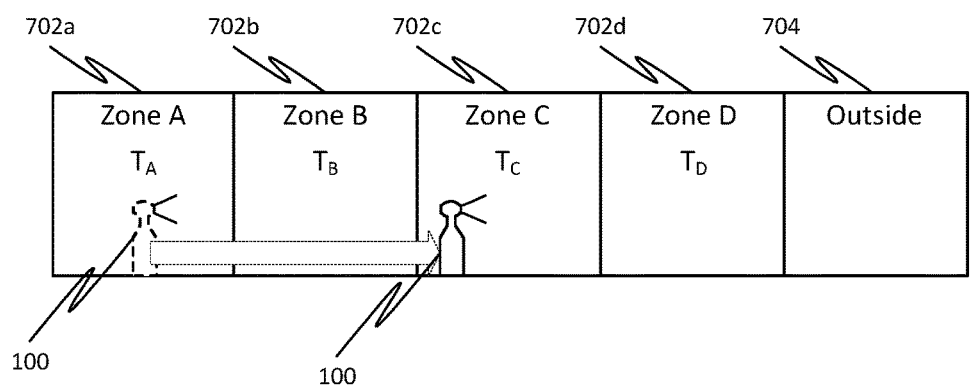
FIG. 7 illustrates the operation of a comfort unit to effect space shifting of thermal load within an environment, according to one or more embodiments of the disclosed subject matter.

Second, thermal loads can be space shifted. In this scenario, the central control system coordinates one or more of the comfort units physically move to a particular zone in the building that may be over or under conditioned, thereby shifting the thermal load in a spatial sense. Such a scenario is illustrated schematically in FIG. 7. Thus, a comfort unit 100 may start out in a first zone 702a where it provides a microenvironment around the user within the zone 702a. For example, when operating in a cooling mode of operation, the comfort unit 100 may store waste heat in an onboard TSM. After the onboard TSM of the comfort unit 100 has been expended, the central control system may direct the comfort unit 100 to a different zone, for example, zone 702c where a temperature $T_C$ thereof is less than a temperature $T_A$ of zone 702a. The difference in temperature may be due to over conditioning of zone 702c, for example, due to differential load or other imbalances in the system. Once in zone 702c, the comfort unit 100 may release the heat stored in its TSM thereby raising the temperature of zone 702c. Alternatively or additionally the comfort unit 100 may move to an outdoor location 704 and release its heat there to avoid any change in the building environment. For example, the stored heat may be released from the TSM via an exhaust port or through reverse operation of the comfort unit (i.e., to provide heating in zone 702c when it previously provided cooling in zone 702a).

This ability of the comfort unit to physically move between zones of the building and to communicate with central control system allows the central control system, in particular a control algorithm thereof, to shift thermal loads in a short time period between over and under addressed thermal zones of the building. Moreover, the environmental control system can control when and where stored heat can be released most efficiently and effectively and taking into account zone conditions, outdoor conditions, and building occupancy. The release of stored heat to the ambient environment or to the outdoor environment can be effective to recharge/regenerate the TSM for further use by the comfort unit in providing the desired microenvironment for the user. When ambient temperature is insufficient to recharge the TSM, building HVAC systems can be turned on to assist the recharging process.

In addition to the time shifting and space shifting noted above, embodiments of the disclosed subject matter also provide for recharging of the TSM of the comfort unit 100 once it is expended, which recharging may be independent of any time or space shifting needs. As used herein, recharging refers to changing a temperature and/or phase of the TSM so that is once again immediately usable by the comfort unit for creating a microenvironment for the user. In some embodiments, such recharging/regeneration of the TSM may occur at a separate charging station 806, as illustrated schematically in FIG. 8A.

Comfort unit 802a can operate to provide the desired microenvironment 614 to a user 612 until its onboard TSM is expended. At this point, the comfort unit 802a would be unable to maintain the desired microenvironment 614 or would have to release energy stored in the TSM in order to continue operation. Comfort unit 802a can thus proceed to a charging station 806 within the environment 616, where a charge connection 808 can interface with a recharge port 804 on the comfort unit to recharge the TSM, for example, by changing a temperature and/or phase thereof. Simultaneously, the charging station 806 may charge an onboard battery of the comfort unit. The charging station 806 may serve one comfort unit 802*b* at a time, or multiple comfort units at a time.

Figure 8A:
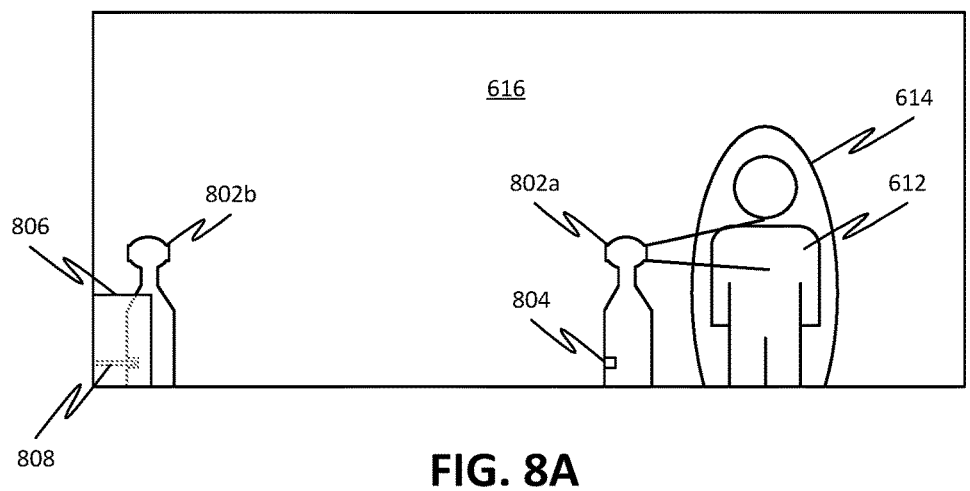
FIG. 8A illustrates the operation of a comfort unit to provide recharging of a thermal storage material therein, according to one or more embodiments of the disclosed subject matter.
Figure 8B:
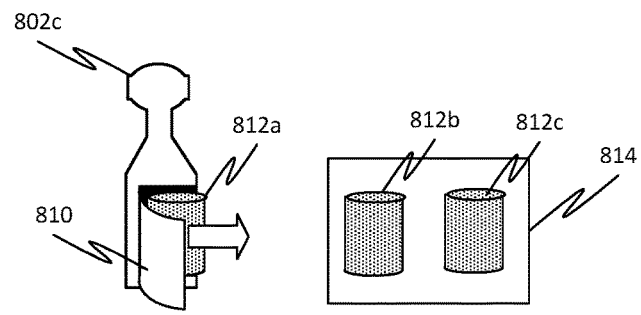
FIG. 8B illustrates the operation of a comfort unit with removable PCM for recharging via a separate charge station, according to one or more embodiments of the disclosed subject matter.
Figure 8C:
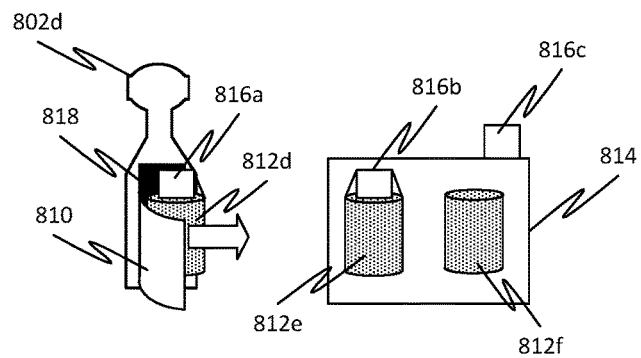
FIG. 8C illustrates the operation of the comfort unit with removable PCM-heat pump for substitution or recharging, according to one or more embodiments of the disclosed subject matter.

Although a particular configuration for recharging of the comfort unit 100 has been illustrated in FIG. 8A, other configurations are also possible according to one or more contemplated embodiments. For example, the onboard TSM can be held in the comfort unit in a removable canister or container. Once the TSM has been expended, the canister can be removed and transported to a separate recharging or storage station, and replaced with a new canister. Alternatively or additionally, the TSM can be removed to change modes of operation, for example, when an TSM used in a heating mode is different than the TSM used in a cooling mode. Such a configuration is illustrated in FIG. 8B, where an expended TSM cartridge 812*a* is removed via access door 810 of comfort unit 802*c* and can be replaced with a recharged TSM cartridge 812*b* or a different stored TSM cartridge 812*c* held at a charging/storage station 814.

In another example, the onboard TSM 812*d* and the heat pump 816*a* are both removable from the comfort unit 802*d* and can be removed/replaced separately or together. For example, the TSM 812*d* and the heat pump 816*a* can be together in a common housing 818 that can be removed via access door 810. A new unit, for example with a fully charged TSM 812*e* and heat pump 816*b*, can be inserted into the comfort unit 802*d*. As with the embodiment of FIG. 8B, the TSM can be replaced with a different TSM 812*f* and/or a different heat pump 816*c*, for example, to change a mode of operation. Because the entire heat pump and TSM can be swapped from the comfort unit, a seal between the TSM and a heat exchanger of the heat pump may be improved.

In yet another example, the comfort unit itself can include an onboard regeneration module, for example, a separate vapor compression system that only runs during certain times to recharge the TSM once it is depleted. For example, in some embodiments, the VCS may operate to provide on-board regeneration of the TSM. For example, the VCS may operate in a first mode of operation to store heat in the TSM. In the second mode of operation, the VCS may be turned into a thermosiphon. The heat stored in the TSM can be released to the ambient environment via the heat exchanger of the VCS, whereby the working fluid of the VCS is driven by a density difference caused by the temperature differential between the TSM and the cooler ambient environment.

Figure 9A:
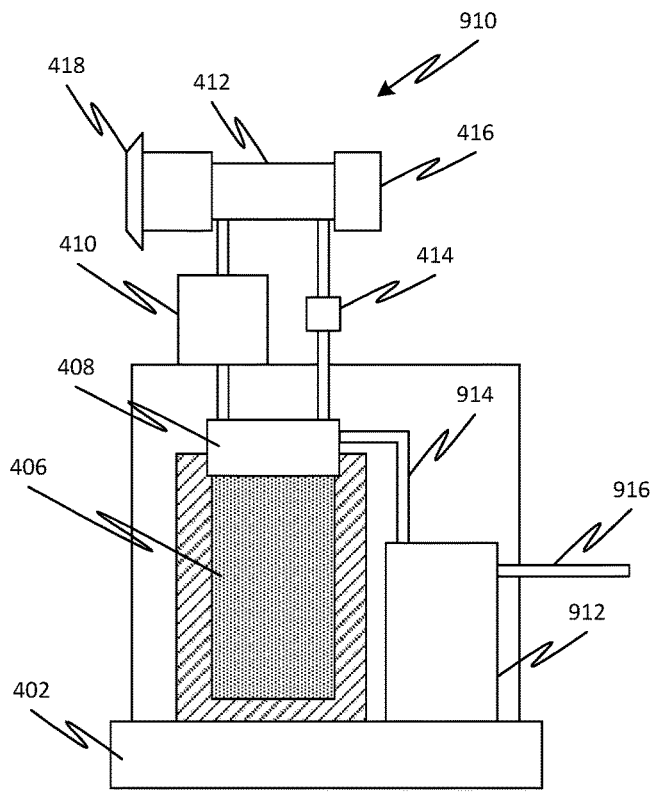
FIG. 9A shows another comfort unit that can provide dehumidification, according to one or more embodiments of the disclosed subject matter.

Although configurations of the comfort unit, in particular a comfort unit employing a PCM for heating or cooling, have been discussed above, embodiments of the disclosed subject matter are not limited thereto. Rather, other configurations are also possible according to one or more contemplated embodiments. For example, the comfort unit may be configured to switch between sensible cooling mode and a dehumidification mode. FIG. 9A shows a simplified cross-sectional view of a comfort unit 910 that may provide such functions. Some features of comfort unit 910 are similar to those of the comfort unit 400 of FIG. 4A. Accordingly, only those features that are different from FIG. 4A will be discussed below.

In FIG. 9A, the comfort unit 910 operates during a cooling mode of operation to store heat from the air in TSM 406 via heat exchanger 408. During the dehumidification mode of operation, water condensing in one of heat exchangers 408, 412 can be conveyed via conduit 914 to a condensation tank 912, where it can be stored for later use, such as drinking, irrigation, supplementing a building supply, or any other use. The stored water may be removed from the condensation tank 912, for example, via optional port/outlet 916.

Figure 9B:
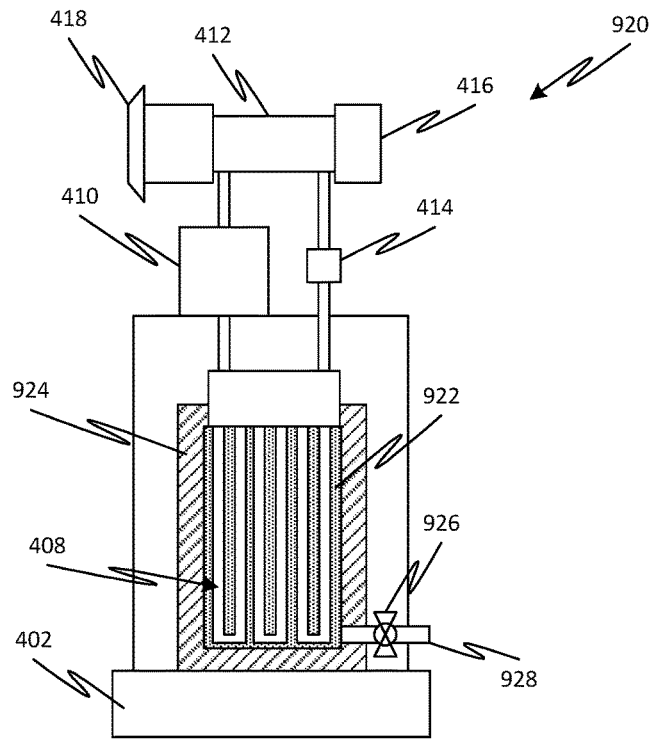
FIG. 9B shows another comfort unit using a single phase thermal storage material, according to one or more embodiments of the disclosed subject matter.

In FIG. 9B, a simplified cross-sectional view of another comfort unit 920 where the TSM comprises a non-PCM material, for example, a single phase (or substantially single phase) liquid or solid material, such as metal or water (or ice water). Some features of comfort unit 920 are similar to those of comfort unit 400 of FIG. 4A. Accordingly, only those features that are different from FIG. 4A will be discussed below.

The comfort unit 920 includes an insulating container 924 that holds a single phase material 922 therein, and with heat exchanger 408 in thermal contact with the single phase material 922. Heat transferred with the heat exchanger 408 can be stored in (or extracted from) the single phase material 922 by changing a temperature thereof. When the single phase material 922 is a liquid, inlet/outlet 928 with access valve 926 can be used to add/remove the liquid from the container 924.

For example, when the single phase material 922 is chilled or ice water, the comfort unit 920 can provide a cooling microenvironment. The chilled water can be obtained from either existing building infrastructure (e.g., an HVAC system) or from a standalone water chilling station. After use in providing the microenvironment, the now warm water may be sent back to the building chiller system to conserve water. For open water systems, tap water may be used in the evaporator to provide cool air. In another example, when the single phase material 922 is hot water, the comfort unit 920 can provide a heating microenvironment. The hot water can be obtained from either existing building infrastructure (e.g., a hot water heater) or from a standalone water heating station.

Figure 9C:
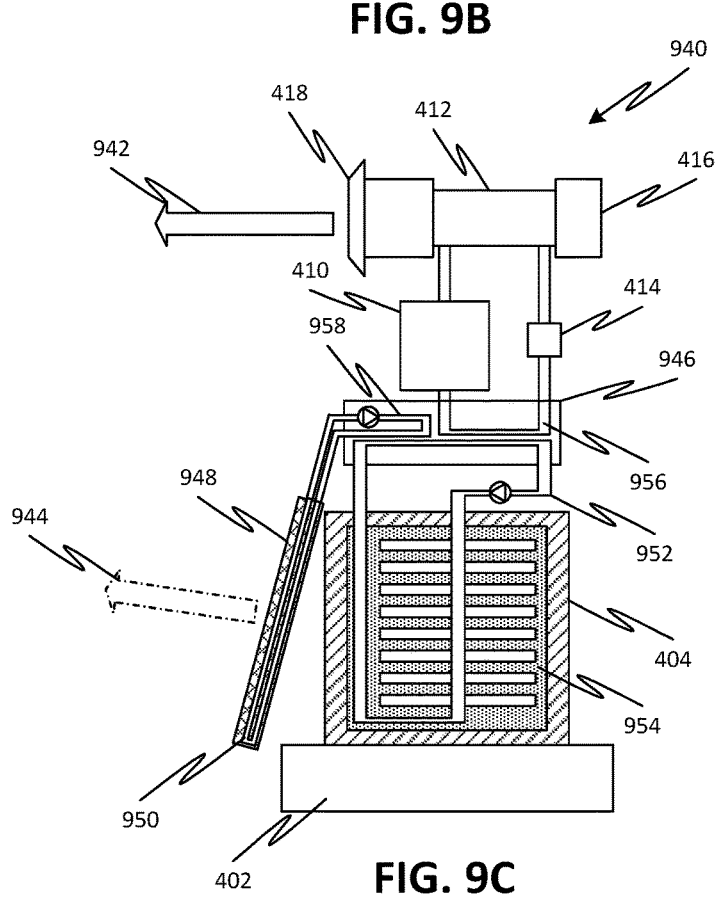
FIG. 9C shows another comfort unit employing radiative panels, according to one or more embodiments of the disclosed subject matter.

In FIG. 9C, a simplified cross-sectional view of a comfort unit 940 that uses a radiation panel 948 in addition to, or in place of, an TSM 954 is shown. Some features of comfort unit 940 are similar to those of comfort unit 400 of FIG. 4A. Accordingly, only those features that are different will be discussed below.

As with previous configurations, heat is transferred between the air and a heat exchanger 946 via heat pump fluid loop 956. However, heat exchanger 946 may be in thermal communication with radiative panel 948 via fluid loop 958 in addition to (or in place of) TSM 954 via fluid loop 952. Radiative panel fluid loop 958 can include one or more fluid conduits 950, that may circulate refrigerant (or other fluid) along a back region of the radiative panel 948 to control a temperature thereof. Thus, in addition to the cooling or heating air flow 942 from nozzle 418, a radiation panel 948 provides radiative heat transfer 944 to the user. The radiative heat transfer may provide improved thermal comfort than forced convection alone.

Although the radiative panel 948 is illustrated as a single contiguous panel, embodiments are not limited thereto. Indeed, multiple connected or independent radiative panels may be provided on the same comfort unit. In an example, the radiative panel may be segmented. In another example, different radiative panels may operate to provide different temperatures, such as a warmer temperature to heat lower extremities of a user while other radiative panels and/or the air nozzle 418 provide a cooling effect to the upper body of the user.

Figure 9D:
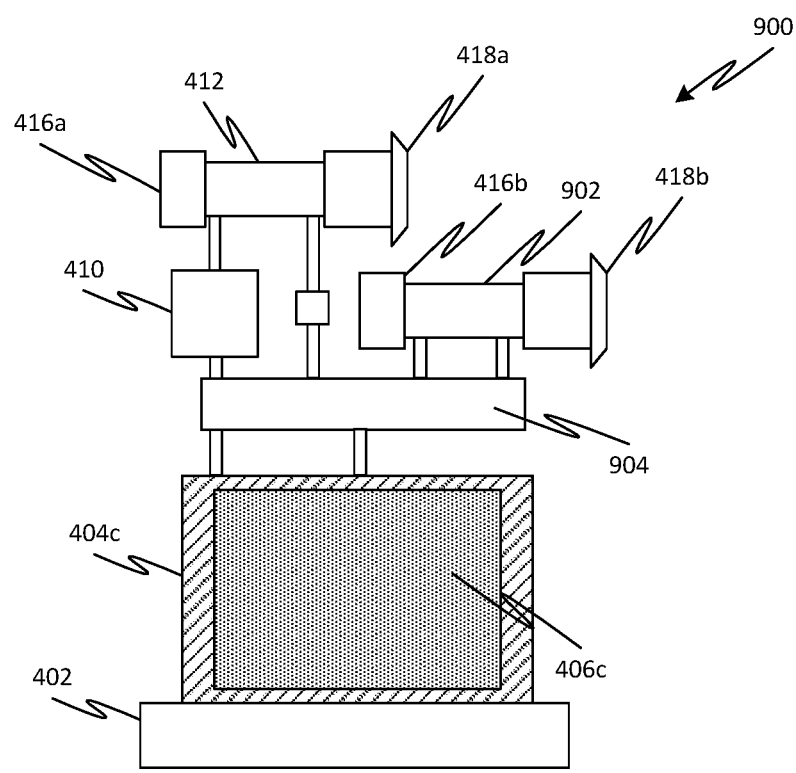
FIG. 9D shows another comfort unit having a vapor compression system capable of providing simultaneous heating and cooling, according to one or more embodiments of the disclosed subject matter.

FIG. 9D illustrates yet another configuration of a comfort unit 900, where multiple nozzles 418*a*, 418*b* can provide independent heating and cooling of a user (or multiple users) at the same time. Some features of the comfort unit 900 are similar to those of comfort unit 400 of FIG. 4A. Accordingly, only those features that are different from FIG. 4A will be discussed below.

In FIG. 4A, the first heat exchanger 408 only enables a single mode of operation at a time. In contrast, the comfort unit 900 of FIG. 9D includes a first heat exchanger 904 capable of simultaneously transferring heat to the TSM 406c and transferring heat from TSM 406c, for example, by using separate independent fluid loops (not shown). Such a configuration can allow a user to experience a gradient microenvironment, where different body parts or regions can experience different temperatures. For example, a user's feet can be warmed by air from one nozzle 418b while the user's upper body is cooled by the other nozzle 418a.

Thus, fan 416a can pass air through second heat exchanger 412 to experience a first mode of operation, e.g., to provide a cooling air flow via nozzle 418a. Heat from the air is thus stored in the TSM 406c via heat exchanger 904. At the same time, fan 416b (which may be the same fan as fan 416a, or a separate independent fan) can pass air through heat exchanger 902 to experience a second mode of operation, e.g., to provide a heating air flow via nozzle 418b. Heat from the TSM 406c can be extracted via heat exchanger 904 to heat this air.

Figure 10:
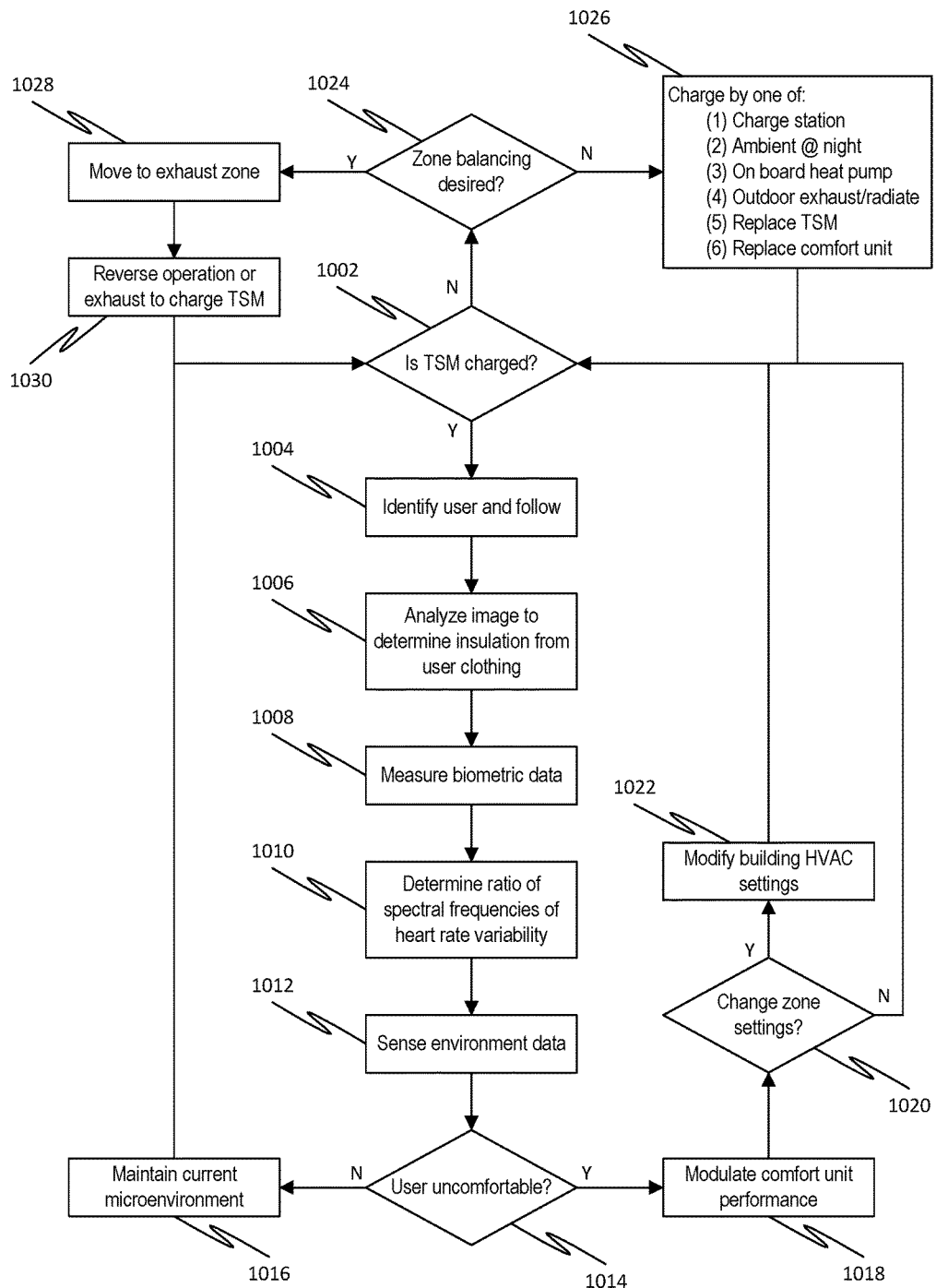
FIG. 10 is a process flow diagram illustrating operational aspects of an environmental control unit, including the comfort unit, according to one or more embodiments of the disclosed subject matter.

FIG. 10 shows a generalized method for environmental control using one or more control units according to embodiments of the disclosed subject matter. For example, the generalized method may be performed by one or more control units operating independently or in conjunction, such as control module 108, control module 206, and/or central control system 602.

The process can begin at 1002 where it is determined whether the TSM of the control unit is sufficiently charged for a desired mode of operation (e.g., heating, cooling, or dehumidification). If the comfort unit is sufficiently charged, the process proceeds to 1004, where the comfort unit identifies the user. The user can be identified by visual imaging, such as by using facial recognition algorithms. Alternatively or additionally, the user can be identified using a separate device, e.g., a wireless beacon, smart phone, or particular sensing unit, or via contact with the comfort unit, e.g., a fingerprint detector. As an ongoing part of the process beginning at 1004, the comfort unit may track and follow the user as the user moves in the environment.

The process proceeds to 1006, where the user can be imaged, for example, by an IR camera. The image can subsequently be analyzed to determine an insulation level of the user's clothing, as described elsewhere herein. The process proceeds to 1008, where biometric data of the user is obtained. Such biometric data can include heart rate, skin temperature, and skin conductance, and can be obtained using a sensing unit, as described elsewhere herein. The process proceeds to 1010 where the biometric data is processed. Thus, the heart rate data is analyzed to determine a ratio of low spectral frequency heart rate variability to high spectral frequency heart rate variability, as described elsewhere herein. Step 1010 can also include comparing the measured skin temperature and skin conductance to respective predetermined ranges that are indicative of comfort level for the identified user. Thus, different users may have different ranges, and the respective ranges may be adjusted based on particular environmental data. The process proceeds to 1012, where environmental data is obtained. As described elsewhere herein, the environmental data can include air temperature, humidity, turbulence intensity, and/or mean radiant temperature.

Although listed as separate steps, it is of course contemplated that steps 1004-1012 may occur concurrently and/or in any order. For example, since biometric data may be used in the determination of insulation level, step 1008 may precede step 1006. Similarly, since environmental data may be used in the processing of the biometric data, step 1012 may precede step 1010.

The process proceeds to 1014, where it is determined whether the user is comfortable based on the results of steps 1004-1012. For example, the biometric and environmental data can be compiled into a single metric and compared with a single predetermined range for the user to estimate if the user is comfortable. Alternatively or additionally, each piece of data can be separately evaluated to estimate if the user is comfortable. If the user is determined to be comfortable, the process proceeds to 1016, where the current microenvironment climate is maintained and the process repeats at 1002.

If the user is determined to be uncomfortable at 1014, the process proceeds to 1018, where the comfort unit is controlled to change the microenvironment around the user to improve the perceived comfort level. The controlling can include modulating one or more of comfort unit fan speed, operational mode (i.e., heating or cooling), air flow direction, and/or nozzle position. For a cooling mode of operation, the comfort unit may direct the air jet toward a head or upper torso of a user, for example, at an airflow rate in the range of 60 to 80 cubic feet per minute. For a heating mode of operation, the comfort unit may direct the air jet toward the feet or lower extremities of the user, for example, at an airflow rate in the range of 12 to 25 cubic feet per minute.

When the user is located in a building environment with an independent air condition system, the process can proceed to 1020, where it is determined if zone settings should be modified, for example, to save energy, reduce costs, or otherwise improve the comfort level of the user. If modification of zone settings is desired, the process proceeds to 1022 where settings of the building air conditioning system are modified. As described elsewhere herein, the modification of building air conditioning system settings can be a change of at least 4° C. from what would normally be required to maintain a comfortable environment for the user without the comfort unit. As a result, the combined energy usage of the comfort unit and the air conditioning system may be less than if the air conditioning system alone maintained a comfort level of the environment for the user, at least during those periods when the user is present. If there is not independent air conditioning system, if zone setting modification is not desired, or once modification of zone settings is complete, the process return to 1002 for subsequent repetition.

If the comfort unit is not sufficiently charged at 1002 (i.e., the TSM is partially or fully expended), the process proceeds to 1024, where it is determined if recharging via zone balancing (i.e., special shifting) is desired. As explained elsewhere herein, the building can have multiple zones or rooms with the user being located in one of the multiple zones around. After generating the TSM is expended and when zone balancing is desired, the process can move to a desired exhaust zone at 1028. The desired exhaust zone may be another of the multiple zones or rooms where the user or other users may not be, or which may be over or under conditioned. The TSM in the comfort unit can then be recharged at 1030 by releasing heat to or absorbing heat from the empty zone or room. This heat exchange may be by way of an exhaust port coupled to the TSM or by reversing operation of a heat pump of the comfort unit. Once the TSM is recharged, the process can return to 1002 for subsequent repetition.

If at 1024 it is determined that zone balancing is not desired, the process can proceed to 1026, where the TSM can be recharged by any number of mechanisms, as explained elsewhere herein. For example, the TSM can be recharged by physically moving the comfort unit to a charging station, providing heat exchange with an ambient environment in the building when a user is not around (e.g., at night), running an on-board heat pump when a user is not around (e.g., at night), or moving the comfort unit to an outdoor environment for radiative or convective heat transfer. In additional examples, the TSM can be removed from the comfort unit and connected with the charging station, or the TSM can be removed from the comfort unit and replaced with a previously charged or different type of TSM. In still another example, portions (e.g., a combined heat pump and TSM assembly) or the entirety of the comfort unit can be replaced with new portion or a whole new comfort unit to effect the desired recharging. Once the TSM is recharged, the process can return to 1002 for subsequent repetition or until otherwise terminated.

In one or more first embodiments, an environmental control system comprises a comfort unit constructed to create a thermal microenvironment around one or more users. The thermal microenvironment has a temperature different from that of an environment surrounding the microenvironment. The comfort unit comprises a thermal regulation module and an air delivery module. The thermal regulation module heats or cools air for the thermal microenvironment. The air delivery module directs the heated or cooled air to the one or more users to create the thermal microenvironment. The thermal regulation module includes a heat exchanger and a thermal storage material (TSM) thermally coupled to the heat exchanger. The TSM is constructed to store heat therein.

In one or more second embodiments, an environmental control system comprises a multi-function comfort unit constructed to create a thermal microenvironment around one or more users in a first mode of operation and to dehumidify air in a vicinity of the one or more users in a second mode of operation. The thermal microenvironment has a temperature different from that of an environment surrounding the microenvironment. The comfort unit comprises a thermal regulation, an air delivery module, and a condensation tank. The thermal regulation module heats, cools, or dehumidifies air based on the mode of operation. The air delivery module directs the heated or cooled air to the one or more users to create the thermal microenvironment during the first mode of operation. The condensation tank collects water extracted from the air during the second mode of operation. The thermal regulation module includes a heat exchanger and a thermal storage material (TSM) thermally coupled to the heat exchanger. The TSM is constructed to store heat therein.

In one or more variations of the first embodiments, the second embodiments, or any other disclosed embodiment, the environmental control system comprises a port or outlet coupled to the condensation tank for dispensing the collected water for drinking, disposal, or other uses.

In one or more variations of the first embodiments, the second embodiments, or any other disclosed embodiment, the TSM comprises a sensible material of chilled water, heated water, antifreeze, water-glycol mixture, oils, and/or any other secondary working fluid known in the art. In one or more variations of the first embodiments, the second embodiments, or any other disclosed embodiment, the TSM comprises a sensible material of solid or liquid metal. In one or more variations of the first embodiments, the second embodiments, or any other disclosed embodiment, the TSM comprises a phase change material constructed to change phase based on application of a signal thereto and/or transfer of heat. In one or more variations of the first embodiments, the second embodiments, or any other disclosed embodiment, the signal comprises at least one of a voltage signal, a current signal, an ultrasonic signal, and a magnetic signal. In one or more variations of the first embodiments, the second embodiments, or any other disclosed embodiment, the TSM comprises a phase change material (PCM) that stores heat by changing phase.

In one or more variations of the first embodiments, the second embodiments, or any other disclosed embodiment, the environmental control system comprises a sensing unit having one or more sensors that detect biometric data of at least one user, said biometric data comprising heart rate, skin conductance, and/or skin temperature. In one or more variations of the first embodiments, the second embodiments, or any other disclosed embodiment, the sensing unit is constructed to be worn in contact with skin of a user. In one or more variations of the first embodiments, the second embodiments, or any other disclosed embodiment, the sensing unit is constructed as a watch, bracelet, necklace, chest strap, upper arm cuff, or shoe insert to be worn by the user. In one or more variations of the first embodiments, the second embodiments, or any other disclosed embodiment, the sensing unit is constructed as a standalone unit that one or more users touch to allow the detecting of biometric data. In one or more variations of the first embodiments, the second embodiments, or any other disclosed embodiment, the sensing unit is integrated with the comfort unit as a unitary device. In one or more variations of the first embodiments, the second embodiments, or any other disclosed embodiment, the sensing unit comprises a first control module configured to determine a comfort level of the one or more users based on at least the biometric data.

In one or more variations of the first embodiments, the second embodiments, or any other disclosed embodiment, the comfort unit comprises a second control module that controls the thermal regulation module and/or the air delivery module based on a signal from the sensing unit indicative of the determined comfort level to achieve or maintain a desired comfort level. In one or more variations of the first embodiments, the second embodiments, or any other disclosed embodiment, the first control module and the second control module are part of a common control system.

In one or more variations of the first embodiments, the second embodiments, or any other disclosed embodiment, the first control module determines comfort level by calculating a ratio of low spectral frequency heart rate to high spectral frequency rate based on the detected heart rate. In one or more variations of the first embodiments, the second embodiments, or any other disclosed embodiment, the first control module determines comfort level based on a comparison of measured skin temperature and skin conductance to predetermined respective ranges.

In one or more variations of the first embodiments, the second embodiments, or any other disclosed embodiment, the one or more sensors of the sensing unit are further configured to detect air temperature, relative humidity, turbulence intensity, and/or mean radiant temperature. In one or more variations of the first embodiments, the second embodiments, or any other disclosed embodiment, the predetermined respective ranges are adjusted based on the environmental data.

In one or more variations of the first embodiments, the second embodiments, or any other disclosed embodiment, the thermal regulation system has a capacity in a range of 10 W to 3 kW per user, for example, 10-200 W per user.

In one or more variations of the first embodiments, the second embodiments, or any other disclosed embodiment, the thermal regulation module is configured as a vapor compression system (VCS). In one or more variations of the first embodiments, the second embodiments, or any other disclosed embodiment, the heat exchanger is a condenser of the VCS when the thermal regulation module operates in cooling mode. In one or more variations of the first embodiments, the second embodiments, or any other disclosed embodiment, the TSM absorbs waste heat from the condenser and changes temperature and/or phase to store the waste heat therein. In one or more variations of the first embodiments, the second embodiments, or any other disclosed embodiment, the TSM is thermally coupled to the heat exchanger by a fluid loop that is separate from a fluid loop of the VCS.

In one or more variations of the first embodiments, the second embodiments, or any other disclosed embodiment, the TSM at least partially surrounds and is in contact with at least a portion of the heat exchanger.

In one or more variations of the first embodiments, the second embodiments, or any other disclosed embodiment, the environmental control system comprises a switch or valve that reconfigures the VCS to change operation between heating and cooling modes. The heat exchanger is an evaporator of the VCS when the VCS operates in the heating mode, and the TSM discharges heat to the evaporator while changing temperature and/or phase to release the heat stored therein. In one or more variations of the first embodiments, the second embodiments, or any other disclosed embodiment, the switch changes the VCS between a first mode of operation, where heat is stored in the TSM, and a second mode of operation, where the VCS acts as a thermosiphon for regeneration of the TSM, the working fluid of the VCS being driven by a density difference due to a temperature differential between the TSM and the ambient environment.

In one or more variations of the first embodiments, the second embodiments, or any other disclosed embodiment, the VCS and the TSM are in a common housing that is removable from the comfort unit for recharging of the TSM, switching between operation modes, switching to a different TSM, or switching to a different heat pump mechanism.

In one or more variations of the first embodiments, the second embodiments, or any other disclosed embodiment, the TSM is housed in a cassette or container separate from the VCS, the cassette or container being removable from the comfort unit for recharging of the TSM, switching between operation modes, or switching to a different TSM. In one or more variations of the first embodiments, the second embodiments, or any other disclosed embodiment, the TSM is housed in a container having an inner layer and a separate outer layer, the inner layer having different insulation properties than that of the outer layer, wherein the outer layer is detachable from the inner layer so as to change an effective insulation of the container.

In one or more variations of the first embodiments, the second embodiments, or any other disclosed embodiment, the PCM comprises at least one of paraffin, salt hydrate, fatty acid, and water. In one or more variations of the first embodiments, the second embodiments, or any other disclosed embodiment, the PCM comprises a 3-D porous structure, pores of said 3-D porous structure serving as flow paths through which air can flow for heat exchange between the PCM and the air.

In one or more variations of the first embodiments, the second embodiments, or any other disclosed embodiment, the heat exchanger comprises one or more tubes having a diameter less than 2 mm. In one or more variations of the first embodiments, the second embodiments, or any other disclosed embodiment, the heat exchanger is a microchannel heat exchanger. In one or more variations of the first embodiments, the second embodiments, or any other disclosed embodiment, the heat exchanger comprises one or more tubes with radially extending fins, the TSM being in thermal contact with said fins. In one or more variations of the first embodiments, the second embodiments, or any other disclosed embodiment, the heat exchanger comprises one or more metal or plastic inserts that increase a contact area between the TSM and the heat exchanger.

In one or more variations of the first embodiments, the second embodiments, or any other disclosed embodiment, the comfort unit further comprises a robotic platform supporting the thermal regulation module and the air delivery module thereon and configured to move the comfort unit within the environment of the user. In one or more variations of the first embodiments, the second embodiments, or any other disclosed embodiment, the comfort unit further comprises a control module configured to control the robotic platform to follow at least one user within the environment. In one or more variations of the first embodiments, the second embodiments, or any other disclosed embodiment, the comfort unit further comprises a robotic platform supporting the thermal regulation module and the air delivery module thereon and configured to move the comfort unit within the environment of the user. The comfort unit further comprises a control module configured to control the robotic platform to follow at least one user within the environment, and the control module is configured to control the robotic platform responsively to a signal from the sensing unit.

In one or more variations of the first embodiments, the second embodiments, or any other disclosed embodiment, the comfort unit further comprises a robotic platform supporting the thermal regulation module, the air delivery module, and the sensing unit thereon and configured to move the comfort unit and the sensing unit together within the environment. In one or more variations of the first embodiments, the second embodiments, or any other disclosed embodiment, the control module is configured to control the robotic platform responsively to a signal from the sensing unit. In one or more variations of the first embodiments, the second embodiments, or any other disclosed embodiment, the comfort unit further comprises a control module configured to control the robotic platform to follow a predetermined path within the environment.

In one or more variations of the first embodiments, the second embodiments, or any other disclosed embodiment, the air delivery module comprises at least one nozzle, diffuser, and/or slot. In one or more variations of the first embodiments, the second embodiments, or any other disclosed embodiment, the at least one nozzle, diffuser, and/or slot of the air delivery module are adjustable so as to direct air at different locations on a user or at different users. In one or more variations of the first embodiments, the second embodiments, or any other disclosed embodiment, the comfort unit further comprises a control module configured to control the air delivery module to adjust the at least one nozzle, diffuser, and/or slot. In one or more variations of the first embodiments, the second embodiments, or any other disclosed embodiment, the control module is configured to adjust the at least one nozzle, diffuser, and/or slot such that in a cooling mode of the comfort unit the cooled air is directed at an upper portion of the user and such that in a heating mode of the comfort unit the heated air is directed at a lower portion of the user.

In one or more variations of the first embodiments, the second embodiments, or any other disclosed embodiment, a charging station for recharging the comfort unit, wherein the charging station is configured to change the temperature and/or phase of the TSM when the comfort unit is coupled thereto. In one or more variations of the first embodiments, the second embodiments, or any other disclosed embodiment, the charging station is also configured to charge a battery of the comfort unit. In one or more variations of the first embodiments, the second embodiments, or any other disclosed embodiment, the environmental control system comprises a charging station configured to recharge the TSM by changing its temperature and/or phase when a removable container or a removable cartridge that houses the TSM is coupled to the charging station.

In one or more variations of the first embodiments, the second embodiments, or any other disclosed embodiment, the comfort unit further comprises an onboard regeneration module that changes a temperature or phase of the TSM, the TSM providing heating or cooling of air flowing through the heat exchanger. In one or more variations of the first embodiments, the second embodiments, or any other disclosed embodiment, the onboard regeneration module comprises a vapor compression system.

In one or more variations of the first embodiments, the second embodiments, or any other disclosed embodiment, the comfort unit comprises one or more sensors that detect air temperature, relative humidity, turbulence intensity, and/or mean radiant temperature. In one or more variations of the first embodiments, the second embodiments, or any other disclosed embodiment, the comfort unit comprises a camera configured to obtain one or images of the user. In one or more variations of the first embodiments, the second embodiments, or any other disclosed embodiment, the comfort unit comprises a control module coupled to the camera and configured to perform a facial recognition of the user from the one or more images. In one or more variations of the first embodiments, the second embodiments, or any other disclosed embodiment, wherein the camera is an infrared (IR) camera. In one or more variations of the first embodiments, the second embodiments, or any other disclosed embodiment, the comfort unit comprises a control module coupled to the IR camera and configured to determine thermal insulation and/or clothing worn by the user from the one or more images.

In one or more variations of the first embodiments, the second embodiments, or any other disclosed embodiment, the comfort unit further comprises one or more of an air purification module that filters contaminants from air for the microenvironment, an air ionization module that ionizes air for the microenvironment, a dehumidification module that removes water from air for the microenvironment, a humidification module that adds water to air for the microenvironment, a home monitoring/security module that comprises one or more sensors and monitors the environment to alert the user, a physical storage compartment for use by the user.

In one or more variations of the first embodiments, the second embodiments, or any other disclosed embodiment, the environmental control system comprises an air conditioning unit that regulates a temperature of said environment. The air conditioning unit maintains the temperature of the environment different from that of the thermal microenvironment. In one or more variations of the first embodiments, the second embodiments, or any other disclosed embodiment, wherein the maintained temperature of the environment is at least 4° C. above or below the temperature of the thermal microenvironment. In one or more variations of the first embodiments, the second embodiments, or any other disclosed embodiment, the environmental control system comprises a central control unit that controls at least the air conditioning unit, and the central control unit adjusts the temperature of the environment based on overall energy usage and signals from the sensing unit and/or the comfort unit. In one or more variations of the first embodiments, the second embodiments, or any other disclosed embodiment, the control modules of the comfort unit and/or the sensing unit are part of the central control unit, the central control unit controlling operation of the comfort unit in addition to the air conditioning unit.

In one or more variations of the first embodiments, the second embodiments, or any other disclosed embodiment, the comfort unit further comprises one or more panels constructed for radiative heat transfer with the one or more users. In one or more variations of the first embodiments, the second embodiments, or any other disclosed embodiment, each panel comprises one or more conduits with fluid flowing therein to regulate a surface temperature of the panel to effect the radiative heat transfer, said fluid transferring heat with the TSM via said heat exchanger or a different heat exchanger.

In one or more variations of the first embodiments, the second embodiments, or any other disclosed embodiment, the air delivery module is constructed to direct the heated or cooled air to each user individually and serially. In one or more variations of the first embodiments, the second embodiments, or any other disclosed embodiment, the air delivery module comprises a swinging or oscillating air outlet.

In one or more variations of the first embodiments, the second embodiments, or any other disclosed embodiment, the air delivery module is constructed to direct the heated or cooled air to each user simultaneously.

In one or more variations of the first embodiments, the second embodiments, or any other disclosed embodiment, the air delivery module comprises an adjustable telescoping portion that can change a distance between a user and an outlet of the heated or cooled air.

In one or more third embodiments, an environmental control method comprises detecting a comfort level of one or more users in an environment having a first temperature, and based on the detected comfort level, generating a microenvironment around the one or more users using a comfort unit. The microenvironment has at least one of temperature and humidity different from that of the environment, and the comfort level of at least one user is improved by the generated microenvironment.

In one or more variations of the third embodiments or any other disclosed embodiment, the comfort unit comprises a thermal regulation module that conditions air for the microenvironment, and the conditioning of the air comprises at least one of heating, cooling, humidification, or dehumidification. In one or more variations of the third embodiments or any other disclosed embodiment, the thermal regulation module comprises a heat exchanger and a thermal storage material (TSM) thermally coupled to the heat exchanger. In one or more variations of the third embodiments or any other disclosed embodiment, the TSM comprises at least one of chilled water, heated water, solid metal, liquid metal, and a phase change material (PCM).

In one or more variations of the third embodiments or any other disclosed embodiment, the method comprises, in a cooling mode of the thermal regulation module, storing waste heat in the TSM. In one or more variations of the third embodiments or any other disclosed embodiment, the method comprises, in a heating mode of the thermal regulation module, using heat stored in the TSM to heat air. In one or more variations of the third embodiments or any other disclosed embodiment, the method comprises, in a dehumidification mode of the thermal regulation module, storing waste heat in the TSM.

In one or more variations of the third embodiments or any other disclosed embodiment, the method comprises, prior to said generating the microenvironment, charging the TSM by changing a temperature or phase thereof. In one or more variations of the third embodiments or any other disclosed embodiment, the method comprises, prior to the charging, at least one of moving the comfort unit to a charging station, moving the comfort unit to a separate zone or room, moving the comfort unit to an outdoor environment for radiative heat transfer, and removing the TSM from the comfort unit and connecting with a charging station.

In one or more variations of the third embodiments or any other disclosed embodiment, the method comprises, prior to or after said generating the microenvironment, at least one of removing the TSM from the comfort unit and replacing with a previously charged TSM, removing the TSM from the comfort unit and replacing with a different type of TSM that is charged, and removing the TSM and a corresponding heat pump from the comfort unit and replacing with a different type of TSM and/or a different type of heat pump.

In one or more variations of the third embodiments or any other disclosed embodiment, the comfort unit comprises an air delivery module that directs the conditioned air to the one or more users to create the microenvironment.

In one or more variations of the third embodiments or any other disclosed embodiment, the detecting a comfort level of the one or more users comprises measuring biometric data of at least one user. The biometric data includes at least one of heart rate, skin conductance, and/or skin temperature. In one or more variations of the third embodiments or any other disclosed embodiment, the detecting a comfort level of the one or more users comprises determining a ratio of low spectral frequency heart rate to high spectral frequency heart rate. In one or more variations of the third embodiments or any other disclosed embodiment, the detecting a comfort level of the one or more users comprises generating a signal indicating that the one or more users are uncomfortable when the ratio exceeds a predetermined threshold.

In one or more variations of the third embodiments or any other disclosed embodiment, the detecting a comfort level of the one or more users comprises detecting environmental data of the environment or a pre-existing microenvironment. The environmental data comprises at least one of air temperature, relative humidity, turbulence intensity, and mean radiant temperature.

In one or more variations of the third embodiments or any other disclosed embodiment, the comfort level comprises a metric based on the detected biometric and environmental data. In one or more variations of the third embodiments or any other disclosed embodiment, the comfort unit generates the microenvironment responsive to a signal indicative of the comfort level metric, and the comfort unit controls the microenvironment to maintain the comfort level metric within a predetermined range corresponding to a temperature or humidity level where at least one user is comfortable.

In one or more variations of the third embodiments or any other disclosed embodiment, the detecting the comfort level comprises obtaining an infrared image of at least one user, and analyzing the image to determine an amount of clothing insulation of the at least one user.

In one or more variations of the third embodiments or any other disclosed embodiment, the method further comprises, prior to the detecting a comfort level, imaging the one or more users, and analyzing the image to identify at least one user. In one or more variations of the third embodiments or any other disclosed embodiment, the analyzing comprises using facial recognition algorithms.

In one or more variations of the third embodiments or any other disclosed embodiment, the method comprises controlling the comfort unit to automatically follow at least one user as said user moves in the environment.

In one or more variations of the third embodiments or any other disclosed embodiment, the environment is an interior of a building that has a separate air conditioning unit to regulate a temperature and/or humidity of said environment. In one or more variations of the third embodiments or any other disclosed embodiment, the method further comprises controlling the air conditioning unit such that a temperature and/or humidity of said environment is maintained at a level different from the microenvironment. In one or more variations of the third embodiments or any other disclosed embodiment, the controlling is such that a combined energy usage of the comfort unit and the air conditioning unit is less than if the air conditioning unit alone maintained a temperature or humidity level of the environment at the temperature or humidity level of the microenvironment. In one or more variations of the third embodiments or any other disclosed embodiment, a temperature difference between the environment and the microenvironment is at least 4° C.

In one or more variations of the third embodiments or any other disclosed embodiment, the building comprises multiple zones or rooms, the one or more users being located in one of the multiple zones or rooms. In one or more variations of the third embodiments or any other disclosed embodiment, the method further comprises after the generating the microenvironment, controlling the comfort unit to move to another of the multiple zones or rooms. In one or more variations of the third embodiments or any other disclosed embodiment, the method further comprises recharging a thermal storage material (TSM) in the comfort unit by releasing heat from the TSM to the another of the multiple zones or rooms, or absorbing heat from the another of the multiple zone or rooms in the TSM.

In one or more variations of the third embodiments or any other disclosed embodiment, the building includes a supply of hot water or chilled water. In one or more variations of the third embodiments or any other disclosed embodiment, the method further comprises after the generating the microenvironment, replacing expended water in the comfort unit with hot water or chilled water from said building supply.

In one or more variations of the third embodiments or any other disclosed embodiment, the generating the microenvironment based on the detected comfort level comprises modulating at least one of air flow rate from the comfort unit, temperature of air from the comfort unit, outlet location of air from the comfort unit, and a flow direction of air from the comfort unit. In one or more variations of the third embodiments or any other disclosed embodiment, in a heating mode of the comfort unit, the air flow from the comfort unit is directed toward feet of at least one user. In one or more variations of the third embodiments or any other disclosed embodiment, in a cooling mode of the comfort unit, the air flow from the comfort unit is directed toward a head or upper torso of at least one user.

In one or more variations of the third embodiments or any other disclosed embodiment, the method comprises collecting water removed from air during the generating the microenvironment in a condensation tank onboard the comfort unit.

In one or more variations of the third embodiments or any other disclosed embodiment, the comfort unit comprises at least one radiative panel, and the generating the microenvironment comprises controlling a temperature around at least one user using radiation from the radiative panel. In one or more variations of the third embodiments or any other disclosed embodiment, the generating the microenvironment comprises passing air from the environment through a phase change material (PCM) constructed as a porous 3-D matrix so as to exchange heat between the PCM and the air. In one or more variations of the third embodiments or any other disclosed embodiment, the generating the microenvironment comprises simultaneously delivering heated air and cooled air via the comfort unit. In one or more variations of the third embodiments or any other disclosed embodiment, the generating the microenvironment employs a heat pump onboard the comfort unit. In one or more variations of the third embodiments or any other disclosed embodiment, the heat pump is configured as a vapor compression system.

It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The foregoing descriptions apply, in some cases, to examples generated in a laboratory, but these examples can be extended to production techniques. Thus, where quantities and techniques apply to the laboratory examples, they should not be understood as limiting.

It is thus apparent that there is provided in accordance with the present disclosure, comfort units, and systems, methods, and devices for use thereof. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. An environmental control system comprising:
   a comfort unit constructed to create a thermal microenvironment around one or more users, the thermal microenvironment having a temperature different from that of an environment surrounding the microenvironment, the comfort unit comprising:
      a thermal regulation module that cools air for the thermal microenvironment;
      an air delivery module that directs the cooled air to the one or more users to create the thermal microenvironment; and
      a first control module that controls the thermal regulation module and the air delivery module according to at least first and second modes of operation,
   wherein the thermal regulation module includes a heat pump system and a thermal storage material (TSM),
   wherein the heat pump system includes a first heat exchanger, a second heat exchanger, a compressor, and an expansion valve connected together by a working fluid loop,
   wherein the TSM is constructed to store heat therein and is thermally coupled to the first heat exchanger,
   wherein the air delivery module is thermally coupled to the second heat exchanger, and
   wherein the first control module controls the thermal regulation module and the air delivery module such that:
      in the first mode of operation to cool the air for the thermal microenvironment, the heat pump system is configured as a vapor compression system (VCS) with the first heat exchanger acting as a condenser of the VCS, the VCS stores waste heat from the condenser in the TSM, and the TSM changes temperature and/or phase to store the waste heat therein, and
      in the second mode of operation to recharge the TSM, the heat pump system is configured as a thermosiphon such that heat stored in the TSM is released via the first heat exchanger and working fluid in the working fluid loop is passively driven by a density difference due to a temperature differential between the TSM and the environment.

2. The environmental control system of claim 1, further comprising a sensing unit having one or more sensors that detect biometric data of at least one user, said biometric data comprising heart rate, skin conductance, and/or skin temperature.

3. The environmental control system of claim 2,
   wherein the sensing unit comprises a second control module configured to determine a comfort level of the one or more users based on at least the biometric data, and
   wherein the second control module determines comfort level by at least one of:
      calculating a ratio of low spectral frequency heart rate to high spectral frequency heart rate based on the detected heart rate, and
      by comparing skin temperature and skin conductance to respective predetermined ranges.

4. The environmental control system of claim 2, wherein the sensing unit comprises a first control module configured to determine a comfort level of the one or more users based on at least the biometric data.

5. The environmental control system of claim 1, wherein the heat pump system and the TSM are in a common housing that is removable from the comfort unit for recharging of the TSM, switching between operation modes, switching to a different TSM, or switching to a different heat pump mechanism.

6. The environmental control system of claim 1, wherein the TSM is housed in a cassette or container separate from the heat pump system, the cassette or container being removable from the comfort unit for recharging of the TSM, switching between operation modes, or switching to a different TSM.

7. The environmental control system of claim 1, wherein the TSM is housed in a container having an inner layer and a separate outer layer, the inner layer having different insulation properties than that of the outer layer, wherein the outer layer is detachable from the inner layer so as to change an effective insulation of the container.

8. The environmental control system of claim 1,
   wherein the TSM comprises a phase change material (PCM) that stores heat by changing phase, and
   wherein the PCM comprises a 3-D porous structure, pores of said 3-D porous structure serving as flow paths through which air can flow for heat exchange between the PCM and the air.

9. The environmental control system of claim 1, wherein the first heat exchanger comprises one or more tubes with radially extending fins, the TSM being in thermal contact with said fins, or the first heat exchanger comprises one or more metal or plastic inserts that increase a contact area between the TSM and the first heat exchanger.

10. The environmental control system of claim 1, further comprising a charging station for recharging the comfort unit, wherein the charging station is configured to change the temperature and/or phase of the TSM when the comfort unit is coupled thereto.

11. The environmental control system of claim 10, wherein the charging station is also configured to charge a battery of the comfort unit.

12. The environmental control system of claim 1, further comprising a charging station configured to recharge the TSM by changing its temperature and/or phase when a removable container or a removable cartridge that houses the TSM is coupled to the charging station.

13. The environmental control system of claim 1, further comprising:
   an air conditioning unit that regulates a temperature of said environment,
   wherein the air conditioning unit maintains the temperature of the environment different from that of the thermal microenvironment.

14. The environmental control system of claim 13, wherein the maintained temperature of the environment is at least 4° C. above or below the temperature of the thermal microenvironment.

15. The environmental control system of claim 13, further comprising:
   a central control unit that controls at least the air conditioning unit,
   wherein the central control unit adjusts the temperature of the environment based on overall energy usage and signals from a sensing unit and/or the comfort unit.

16. The environmental control system of claim 1, wherein the comfort unit further comprises a robotic platform supporting the thermal regulation module and the air delivery module thereon and configured to move the comfort unit within the environment of the user.

17. The environmental control system of claim 16, wherein the first control module is configured to control the robotic platform to follow at least one user within the environment.

18. The environmental control system of claim 16, wherein the first control module is configured to control the robotic platform to follow a predetermined path within the environment.

19. The environmental control system of claim 16, further comprising a power storage device that provides power to the comfort unit, the thermal regulation module, the air delivery module, and/or the robotic platform.

20. The environmental control system of claim 1, wherein the comfort unit comprises a camera configured to obtain one or more images of the user, and the camera is an infrared (IR) camera.

21. The environmental control system of claim 20, wherein the first control module is coupled to the IR camera and configured to determine thermal insulation and/or clothing worn by the user from the one or more images.

22. The environmental control system of claim 1, wherein the comfort unit comprises:
    a camera configured to obtain one or more images,
        wherein the first control module is configured to detect at least a portion of the user from the one or more images.

23. The environmental control system of claim 1, wherein the environmental control system is constructed as a portable, self-contained device that provides the heating or cooling without contemporaneous venting.

* * * * *